United States Patent [19]
LaVoie et al.

[11] Patent Number: 5,981,541
[45] Date of Patent: Nov. 9, 1999

[54] SUBSTITUTED HETEROCYCLES AS ANTI-TUMOR AGENTS

[75] Inventors: Edmond J. LaVoie, Princeton Junction; Leroy Fong Liu, Bridgewater; Darshan B. Makhey, Higland Park, all of N.J.

[73] Assignee: Rutgers, The State University of New Jersey, New Brunswick, N.J.

[21] Appl. No.: 08/935,777

[22] Filed: Sep. 23, 1997

Related U.S. Application Data

[60] Provisional application No. 60/026,511, Sep. 23, 1996.

[51] Int. Cl.⁶ .......................... C07D 221/18; A61K 31/33
[52] U.S. Cl. .......................... 514/279; 514/280; 514/284; 546/41; 546/48; 546/61
[58] Field of Search ................................. 646/61, 48, 41, 646/36; 514/284, 280, 279

[56] References Cited

U.S. PATENT DOCUMENTS

| | | | |
|---|---|---|---|
| Re. 26,065 | 7/1966 | Marvel et al. | 260/47 |
| 2,915,523 | 12/1959 | Moore et al. | 260/279 |
| 2,981,731 | 4/1961 | Moore et al. | 260/239.1 |
| 2,985,661 | 5/1961 | Hien et al. | 260/309 |
| 3,267,107 | 8/1966 | Sallay et al. | 260/287 |
| 3,272,707 | 9/1966 | Tedeschi et al. | 167/65 |
| 3,449,330 | 6/1969 | Guglielmetti et al. | 260/240 |
| 3,538,097 | 11/1970 | Lowe et al. | 260/268 |
| 3,849,561 | 11/1974 | Iwasa et al. | 424/258 |
| 3,884,911 | 5/1975 | Shimada et al. | 260/240 |
| 4,761,477 | 8/1988 | Ikekawa et al. | 546/48 |
| 4,938,949 | 7/1990 | Borch et al. | 424/10 |
| 4,980,344 | 12/1990 | Maroko | 514/26 |
| 5,106,863 | 4/1992 | Hajos et al. | 514/395 |
| 5,112,532 | 5/1992 | Ninomiya et al. | 252/587 |
| 5,126,351 | 6/1992 | Luzzio et al. | 514/291 |
| 5,190,753 | 3/1993 | Behrens et al. | 424/85.8 |
| 5,244,903 | 9/1993 | Wall et al. | 514/279 |
| 5,318,976 | 6/1994 | Luzzi et al. | 514/279 |
| 5,639,759 | 6/1997 | Magolda et al. | 514/285 |
| 5,646,283 | 7/1997 | Suzuki et al. | 546/61 |

FOREIGN PATENT DOCUMENTS

| | | |
|---|---|---|
| 0496634 | 7/1992 | European Pat. Off. . |
| 1530628 | 12/1989 | Russian Federation . |
| 92/21661 | 12/1992 | WIPO . |

OTHER PUBLICATIONS

Baezner, C., "Uberfuhrung von o–nitround o,p–dinitro–benzylchlorid in acridinderivate", *Berichte der Deutschen Chemischen Gesellschaft*, vol. 37, Weinheim, DE, pp. 3077–3083, (1904).

Baezner, C., et al., "Uberfuhrung von o–nitro– und o,p–dinitro–benzylchlorid in acridinderivate", *Berichte der Deutschen Chemischn Gessellschaft*, vol. 39, pp. 2438–2447, (1906).

Buu–Hoi, N., "The chemistry of carcinogenic nitrogen compounds. Part V. Angular hydroxybenzacridines and hydroxydibenzacridines", *Journal of the Chemical Society*, Letchworth GB, pp. 2096–2099, (1950).

Buu–Hoi, N., et al., "The chemistry of carcinogenic nitrogen compounds. Part X. The Pfitzinger reaction in the synthesis of 1:2 benzacridines", *Journal of the Chemical Society*, Letchworth, GB, pp. 279–281, (1952).

Chen, A.Y., et al., "A New Mammalian DNA Topoisomerase I Poison Hoechst 33342: Cytoxicity and Drug Resistance in Human Cell Cultures", *Cancer Research*, vol. 53, pp. 1332–1337, (Mar. 15, 1993).

Croisy, M., et al., "Synthesis and Carcinogenic Activity of Oxidized Benzacridines: Potential Metabolites of the strong carcinogen 7–Methylbenz[c]acridine and of the inactive isomer 12–methylbenz[a]acridine", *J. Med. Chem*, 26, pp. 303–306, (1983).

Fujii, N., et al., "Induction of Mammalian DNA Topoisomerase I–mediated DNA Cleavage and DNA Winding by Bulgarein", *Journal of Biological Chemistry*, vol. 268, pp. 13160–13165, (1993).

Gandhi, K.K., et al., "Regioselective thermal cyclization of 3–substituted arylenaminoimine hydrochlorides, a convenient method for the synthesis of functionalized polycyclic quinoline derivatives", *Heterocycles*, vol. 41, No. 5, Amsterdam, NL, pp. 911–920, (1995).

Gatto, B., et al. "Identification of Topoisomerase I as the Cytotoxic Target of the Protoberberine Alkaloid Coralyne", *Cancer Research*, vol. 56, pp. 2795–2800, (1996).

Hoan, N., et al., "Syntheses from o–halogenated anisoles and phenetoles", *Chemical Abstracts*, Abstr. No. 6571bg, vol. 41, No. 20, Columbus, Ohio, (Oct. 20, 1947).

(List continued on next page.)

*Primary Examiner*—Richard L. Raymond
*Assistant Examiner*—Deepak R. Rao
*Attorney, Agent, or Firm*—Schwegman, Lundberg, Woessner & Kluth, P.A.

[57] ABSTRACT

The present invention provides compounds of formula (I):

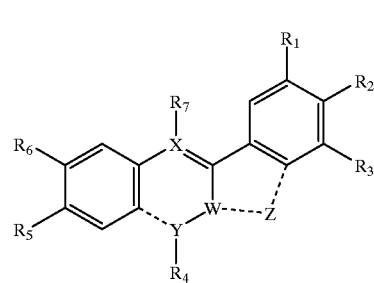

wherein $R_1$–$R_7$, W, X, Y, and Z have any of the values defined in the specification, and pharmaceutically acceptable salt thereof, that are are useful as anticancer agents. Also disclosed are pharmaceutical compositions comprising one or more compounds of formula I, processes for preparing compounds of formula I, and intermediates useful for preparing compounds of formula I.

29 Claims, 4 Drawing Sheets

OTHER PUBLICATIONS

Janin, Y., et al., "Synthesis and Evaluation of New 6–Amino–Substituted Benzo[c]phenanthridine Derivatives" *J. Med. Chem.*, vol. 36, pp. 3686–3692 (1993).

Kametani, T., et al., "Studies on the synthesis of heterocyclic compounds. DCXXVII. The formation of 2,3,9,10–tetramethoxybenz[c]acridine by treatment of 6,7–dimethoxy–1–(4,5–dimethoxy–2–nitrophen ethyl)–2methylisoquinoline with triethyl phosphite", *Chemical and Pharmaceutical Bulletin*, vol. 23, No. 9, pp. 2025–2028, (1975).

Kim, J.S., et al., "Substituted 2,5'–Bi–1H–benzimidazoles: Topoisomerase I Inhibition and Cytotoxicity", *J. Med. Chem.*, vol. 39, 992–998, (1996).

Makhey, D., et al., "Coralyne and Related Compounds as Mammalian Topoisomerase I and Topoisomerase II Poisons", *Bioorg. & Med. Chem. Lett.*, vol. 4, 781–791, (1996).

Makhey, D., et al., "Protoberberine Alkaloids and Related Compounds as Dual Inhibitors of Mammalian Topoisomerase I and II", *Med Chem. Res.*, vol. 5, 1–12, (1994).

Mohanty, M., et al., "New Therapeutic agents of the quinoline series. I. Fused quinolyl compounds", *Chemical Abstracts*, vol. 69, No. 5, p. 1792, (Jul. 29, 1968).

Stermitz, F.R., et al., "Synthesis and Biological Activity of Some Antitumor Benzophenanthridinum Salts", *Journal of Medicinal Chemistry*, vol. 18, pp. 708–713, (1975).

Sun, Q., et al., "Synthesis and Evaluation of Terbenzimidazoles as Topoisomerase I Inhibitors", *J. Med. Chem*, vol. 38, pp. 3638–3644, (1995).

Wang, L., et al., "Inhibition of Topoisomerase I Function by Coralyne and 5,6 –Dihydrocoralyne", *Chem. Res. Toxicol.*, vol. 9, pp. 75–83, (1996).

Wang, L., et al., "Inhibition of Topoisomerase I Function by Nitidine and Fagaronine", *Chem. Res. Toxicol.*, vol. 6, pp. 813–818, (1993).

Yamashita, Y., et al., "Induction of Mammalian DNA Topoisomerase I and II Mediated DNA Cleavage by Saintopin, a New Antitumor Agent from Fungus", *Biochemistry*, vol. 30, pp. 5838–5845, (1991).

Yamashita, Y., et al., "Induction of Mammalian DNA Topoisomerase I Mediated DNA Cleavage by Antitumor Indolocarbazole Derivatives", *Biochemistry*, vol. 31, pp. 12069–12075, (1992).

Badia, D., et al., "Silicon–mediated isoquinoline synthesis: preparation and stereochemical characterization of 4–hydroxy–3–phenylisoquinolines", *Chemical Abstracts*, vol. 117, No. 13, Abstract No. 131034, Tetrahedron; 92, vol. 48 (21), pp. 4419–4430, (Sep. 28, 1992).

Bathini, Y., et al., "Convenient Routes to Substituted Benzimidazoles and Imidazolo[4,5–b]pyridines Using Nitrobenzene as Oxidant", *Synthetic Communications*, 20(7), 955–963, (1990).

Bradsher, C.K., et al., ".alpha–Acyl–o–tolunitriles as intermediates in the preparation of 3–substituted isoquinolines and 1–amino–2–benzopyrylium derivatives", *Chemical Abstracts*, vol. 089, No. 21, Abstract No. 179810, 3817–3820, (1978).

Chen, A.Y., et al., "DNA Minor Groove–Binding Ligands: A Different Class of Mammalian DNA Topoisomerase I Inhibitors", *Proc. Natl. Acad. Sci.*, USA., vol. 90, pp. 8131–8135, (Sep. 1993).

Chen, A.Y., et al., "DNA Topoisomerases: Essential Enzymes and Lethal Targets", *Annu. Rev. Pharmacol. Toxicol.,*, vol. 34, pp. 191–218, (1994).

Cherif, A., et al., "N–(5, 5–Diacetoxypent–1–yl)doxorubicin: A New Intensely Potent Doxorubicin Analogue", *J. Med. Chem.*, 35, 3208–3214, (1992).

D'arpa, P., et al., "Topoisomerase–Targeting Antitumor Drugs", *Biochimica et Biophysica Acta*, 989, 163–177 (1989).

Dominguez, E., et al., "Dehydrogenation reactions of 1–substituted–3–aryltetrahydroisoquin oline derivatives", *Chemical Abstracts*, vol. 101, No. 11, Abstract No. 090742, 525–528, (1984).

Dorofeenko, G.N., et al., "Synthesis of 3–aryl derivatives of 2–benzopyrylium salts with free.alpha–positions", *Chemical Abstracts*, vol. 074, No. 15, Abstract No. 076295, 1013–1014, (1971).

Fitzgerald, J.J., et al., "Reaction of benzocyclobutene oxides with nitriles: synthesis of hypecumine and other 3–substituted isoquinolines", *Chemical Abstracts*, vol. 122, No. 7, Abstract No. 081704, Tetrahedron Lett. ; 94; vol. 35, (49), pp. 9191–4, (Feb. 13, 1995).

Fox, G.J., et al., "para–Bromination of Aromatic Amines: 4–Bromo–N,N–Dimethyl–3–(Trifluoromethyl)Aniline", *Org. Syn.*, 55, 20–23, (1973).

Gallo, R.C., et al., "Studies on the Antitumor Activity, Mechanism of Action, and Cell Cycle Effects of Camptothecin", *Journal of the National Cancer Institute*, 46, 789–795 (Apr. 1971).

Garcia, A., et al., "A simple direct approach to 1–substituted 3–arylisoquinolines from deoxybenzoins and nitriles", *Chemical Abstracts*, vol. 110, No. 25, Abstract No. 231407, Tetrahedron; 88; vol. 44(21);, pp. 6681–6686, (Jun. 19, 1989).

Giovanella, B.C., et al., "Complete Growth Inhibition of Human Cancer Xenografts in Nude Mice by Treatment with 20–(S)—Camptothecin", *Cancer Research*, 51, 3052–3055 (Jun. 1, 1991).

Iwao, M., et al., "A Regiospecific Synthesis of Carbazones via Consecutive Palladium–Catalyzed Cross–coupling and Aryne–Mediated Cyclization", *Heterocycles*, 36, 1483–1488, (1993).

Kim, J.S., et al., "Influence of steric factors on topoisomerase I inhibition and cytotoxicity of bisbenzimidazoles related to Hoechst 33342", Abstract 4, 86th annual meeting of the American Association for Cancer Research, Toronto, Ontario, Canada, 2689, (1995).

Kim, J.S., et al., "Influence of steric factors on topoisomerase I inhibition and cytotoxicity of bisbenzimidazoles related to Hoechst 33342", *Abstract 7, 3rd annual scientific retreat, Cancer Institute of New Jersey, Princeotn Marriott Forrestal Village*, 28, (1995).

Kim, J.S., et al., "Steric factors associated with the topoisomerase I inhibition and cytotoxicity of substituted bisbenzimidazoles", *Abstract 10, American Assn of Pharmaceutical Scientists*, Eastern Regional Meeting, 27, (1995).

Kim, J.S., et al., "Structure–activity Relationships of Benzimidazoles and Related Heterocycles as Topoisomerase I Poisons", *Bioorganic & Med. Chem.*, 4, 621–630, (1996).

Kitamura, T., et al., "Isoquinoline derivatives from the Ritter–type reaction of vinyl cations", *Chemical Abstracts*, vol. 102, No. 1, Abstract No. 006157, Chem. Lett.; 84;(8);, pp. 1351–1354, (Jan. 7, 1985).

LaVoie, E.J., et al., "Structure–activity studies related to minor groove–binding ligands which inhibit mammalian DNA topoisomerase I", *Abstract 1, 85th Annual Meeting of American Association for Cancer Research,* Apr. 10–13, 1994, San Francisco, CA, 2699, (1994).

Meegalla, S.K., et al., "Synthesis and Pharmacological Evaluation of Isoindolo[1,2–b]quinazolinone and Isoindolo[2,1–a]benzimidazole Derivatives Related to the Antitumor Agent Batracylin", *J. Med. Chem.,* 37, 3434–3439, (1994).

Memetzidis, G., et al., "Structure–affinity relationships of berbines or 5,6,13,13a–tetrahydro–8H–dibenzo[a,g]quinolizines at.alpha.–adrenoceptors", *Chemical Abstracts,* vol. 117, No. 3, Abstract No. 019892, Eur. J. Med. Chem.; 91; vol. 26 (6), pp. 605–611, (Jul. 20, 1992).

Nelson, J.T., et al., "Proton and carbon–13 NMR spectra of fifteen substituted isoquinolines", *Chemical Abstracts,* vol. 115, No. 5, Abstract No. 048721, Magn. Reson. Chem.; 91; vol. 29(5), pp. 513–517, (Aug. 5, 1991).

Peters, D., et al., "Synthesis of Various 5–Substituted Uracils", *J. Heterocyclic Chem.,* 27, 2165–2173, (Nov. Dec. 19).

Pilch, D.S., et al., "Biophysical Characterization of a Cytotoxic, Topoisomerase I Poison", *Abstract 8,* 3rd annual Scientific Retreat, Cancer Institute of New Jersey, 3, (1995).

Piper, J.R., et al., "Synthesis and Antifolate Activity of 5–Methyl–5,10–dideaza Analogues of Aminopterin and Folic Acid and an Alternative Synthesis of 5,10–Didaezatetrahydrofolic Acid, a Potent Inhibitor of Glycinamide Ribonucleotide Formyltransferase", *J. Med. Chem.,* 31, 2164–2169, (1988).

Porai–Koshits, B.A., et al., "Imidazole derivatives Synthesis of some polybenzimidazoles", *J. GEn. Chem. USSR,* 23 as related in Chemical Abstracts, vol. 48, Nov. 10, 1954, col. 12740, 873–9, (1953).

Porai–Koshits, B.A., et al., "Imidazole derivatives. Synthesis of some polybenzimidazoles", *Zhur. Obschchei Khim,* 23, as related from Chemical Abstracts, vol. 48, Apr. 25, 1954, col. 4523, 835–41, (1953).

Quast, U., et al., "Heterocyclic.alpha.–carbinolamines with theisoquinuclidine skeleton. 3. Benzoisoquinuclidines", *Chemical Abstracts,* vol. 097, No. 21, Abstract No. 182180, 1501–1508, (1982).

Safaryan, G.P., et al., "2–Benzopyrylium salts. 25, Reaction of 2–benzopyrylium salts with some nucleophiles", *Chemical Abstracts,* vol. 096, No. 17, Abstract No. 142656, 1608–1611, (1982).

Schiess, P., et al., "Thermolytic ring opening of acyloxybenzocyclobutenes: an efficient route to 3–substituted isoquinolines", *Chemical Abstracts,* vol. 104, No. 19, Abstract No. 168332, Tetrahedron Lett.; 85; vol. 26(33), pp. 3959–62, (May 12, 1986).

Shcherbakova, I.V., et al., "2–Benzopyrilium salts.35.Synthesis of the natural alkaloid dehydronorcoralydine and other subsituted salts of dibenzo{a,g] quinolizine", *Chemical Abstracts,* vol. 112, No. 19, abstract No. 179554, Khim,Prir.Soedin.; 89(1), pp. 75–80, (May 7, 1990).

Singh, M.P., et al., "Synthesis and Sequence–Specific DNA Binding of a Topoisomerase Inhibitory Analog of Hoechst 33258 Designed for Altered Base and Sequence Recognition", *Chem. Res. Toxicol.,* 5, vol. 5, 597–607, (1992).

Sotomayor, N., et al., "Oxidation reactions of 2'–functionalized 3–aryltetrahydro–and 3,4–dihydroisoquinolines", *Chemical Abstracts,* vol. 124, No. 11, Abstract No. 145854, Tetrahedron; 95, vol. 51 (46) pp. 12721–30, (Mar. 11, 1996).

Sun, et al., *CA 123:*198740 1995.

Sun, Q., et al., "Structure activity of novel topoisomerase I inhibitors related to Hoechst 33342", *Abstract 6, American Assn of Pharmaceutical Scientists,* Eastern Regional Meeting, 25, (1995).

Sun, Q., et al., "Structure Activity of Topoisomerase I Poisons Related to Hoechst 33342", *Bioorganic & Medicinal Chemistry Letters,,* vol. 4, pp. 2871–2876, (1994).

Sun, Q., et al., "Structure–activity studies related to minor groove–binding ligands which inhibit mammalian DNA topoisomerase I", Cancer Institute of New Jersey, First Annual Scientific Retreat, Jun. 7, 1994, Princeton Marriott Forrestal Village, Princeton, New Jersey, 66, (1994).

Sun, Q., et al., "Synthesis and pharmacological evaluation of a series of novel DNA topoisomerase I inhibitors as antitumor agents", 86th Annual meeting of the American Association for Cancer Research, Toronto, Ontario, Canada, 2688, (1995).

Sun, Q., et al., "Synthesis and Evaluation of Terbenzimidazoles as Topoisomerase I Inhibitors", *J. Med. Chem.,* vol. 38, pp. 3638–3644, (1995).

Sun, Q., et al., "Synthesis and pharmacological evaluation of a series of novel DNA topoisomerase I inhibitors as antitumor agents", 86th Annual meeting of the American Association for Cancer Research, Toronot, Ontario, Canada, 2688, (1995).

Sun, Q., et al., "Synthesis of Benzimidazo[2,1–a]isoquinolines and 5,6–Dihydrobenzimidazo[2,1–a]isoquinolines", *Syn. Lett.,* submitted (1995).

Walterova, D., et al., "Isolation, Chemistry and Biology of Alkaloids from plants of Papaveraceae. Part XCV. Practical application of isotachophoresis in analysis of isoquinoline alkaloids", *Chemical Abstract,* vol. 104, No. 12, No. 95573 Columbus, OH, 23–36, (1986).

Yadagiri, B., et al., "Convenient Routes to Substituted Benzimidazoles and Imidazolo[4,5–b]Pyridines Using Nitrobenzene as Oxidant", *Synthetic Communications,* 20(7), 955–963, (1990).

Yamamoto, Y., et al., "Reaction of 6H–1, 3–oxazin–6–one with benzyne giving isoquinoline derivatives", *Chemical Abstracts,* vol. 118, No. 7, Abstract No. 059563, Annu. rep. Tohoku Coll. Pharm.; 91; vol. 38; 00. 43–45, (Feb. 15, 1993).

Epstein et al., Chemical Abstract 75:96680, 1971.

|   | $R_5$ | $R_6$ | $R_1$ | $R_2$ | $R_3$ |
|---|---|---|---|---|---|
| a | OCH$_3$ | OCH$_3$ | OCH$_3$ | OCH$_3$ | H |
| b | –OCH$_2$O– | | OCH$_3$ | OCH$_3$ | H |
| c | OCH$_3$ | OCH$_3$ | H | H | H |
| d | H | H | OCH$_3$ | OCH$_3$ | H |
| e | OCH$_3$ | OCH$_3$ | H | –OCH$_2$O– | |
| f | OCH$_3$ | OCH$_3$ | H | OCH$_3$ | OCH$_3$ |
| g | OH | OH | OH | OH | H |
| j | OCH$_3$ | OCH$_3$ | H | Cl | H |

SUBSTITUTED HETEROCYCLES AS ANTI-TUMOR AGENTS

PRIORITY OF INVENTION

This application claims priority under 35 U.S.C. §119(e) from U.S. Provisional Application No. 60/026,511, filed Sept. 23, 1996.

U.S. GOVERNMENT RIGHTS

The U.S. Government has certain rights in this invention. This invention was made with the support of Grant No. P41RR0954 awarded by the National Institute of Health, and with the support of Grant CA 39662 awarded by the National Cancer Institute (L.F.L.).

BACKGROUND OF THE INVENTION

DNA-topoisomerases are enzymes which are present in the nuclei of cells where they catalyze the breaking and rejoining of DNA strands, which control the topological state of DNA. Recent studies also suggest that topoisomerases are also involved in regulating template supercoiling during RNA transcription. There are two major classes of mammalian topoisomerases. DNA-topoisomerase-I catalyzes changes in the topological state of duplex DNA by performing transient single-strand breakage-union cycles. In contrast, mammalian topoisomerase II alters the topology of DNA by causing a transient enzyme bridged double-strand break, followed by strand passing and resealing. Mammalian topoisomerase II has been further classified as Type II α and Type II β. The antitumor activity associated with agents which are topoisomerase poisons is associated with their ability to stabilize the enzyme-DNA cleavable complex. This drug-induced stabilization of the enzyme-DNA cleavable complex effectively converts the enzyme into a cellular poison.

Several antitumor agents in clinical use have potent activity as mammalian topoisomerase II poisons. These include adriamycin, actinomycin D, daunomycin, VP-16, and VM-26. In contrast to the number of clinical and experimental drugs which act as topoisomerase II poisons, there are currently only a limited number of agents which have been identified as topoisomerase I poisons. Camptothecin and its structurally-related analogs are among the most extensively studied topoisomerase I poisons. Recently, bi- and terbenzimidazoles (Chen et al., Cancer Res. 1993, 53, 1332–1335; Sun et al., J. Med. Chem. 1995, 38, 3638–3644; Kim et al., J. Med. Chem. 1996, 39, 992–998), certain benzo[c]phenanthridine and protoberberine alkaloids and their synthetic analogs (Makhey et al., Med. Chem. Res. 1995, 5, 1–12; Janin et al., J. Med. Chem 1975, 18, 708–713; Makhey et al., Bioorg. & Med. Chem. 1996, 4, 781–791), as well as the fungal metabolites, bulgarein (Fujii et al., J. Biol. Chem. 1993, 268, 13160–13165) and saintopin (Yamashita et al., Biochemistry 1991, 30, 5838–5845) and indolocarbazoles (Yamashita et al., Biochemistry 1992, 31, 12069–12075) have been identified as topoisomerase I poisons.

The exceptional topoisomerase poisoning observed with coralyne, nitidine, 5,6-dihydro-8-desmethylcoralyne and related analogs prompted several recent studies on those structural features which are associated with their ability to act specifically as poisons of topoisomerase I or topoisomerase II (Gatto et al., Cancer Res. 1996, 56, 2795–2800; Wang et al., Chem. Res. Toxicol. 1996, 9, 75–83; Wang et al., Chem. Res. Toxicol., 1993, 6, 813–818). A common feature associated with all three of these agents is the presence of a 3-phenylisoquinolinium moiety within their structure.

Despite the observation that several of these compounds had similar potency to camptothecin as a topoisomerase I poison or similar potency to VM-26 as a topoisomerase II poison, they possessed only modest cytotoxic activity. The absence of a more direct correlation with their potency as topoisomerase poisons was attributed, in part, to the likelihood that these agents are not likely to be absorbed as effectively into cells as either camptothecin or VM-26. The presence of the quaternary ammonium group most likely impedes cellular uptake. It has been speculated that agents such as coralyne and nitidine may need to undergo hydrolysis to permit effective transport, with subsequent dehydration or cyclodehydration to reform the quaternary ammonium parent compound. This may explain the relatively poor antitumor activity observed in vivo with agents such as coralyne or nitidine.

It is clear that the need exists for anti-cancer agents with improved activity.

SUMMARY OF THE INVENTION

The present invention provides compounds of formula (I):

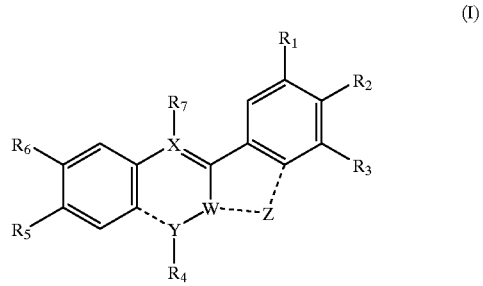

(I)

wherein $R_1$, $R_2$, $R_3$, $R_5$ and $R_6$ are independently H, OH, $NO_2$, $NH_2$, halo, $NHCO(C_1-C_8)$alkyl or $(C_1-C_8)$alkoxy; $R_1$ and $R_2$ together are —$OCH_2O$—; $R_2$ and $R_3$ together are —$OCH_2O$—; or $R_5$ and $R_6$ together are —$OCH_2O$—;

$R_4$ and $R_7$ are independently H, $(C_1-C_8)$alkyl or absent;

W is C or N;

X is C or N;

Y is —C=, —N= or a direct bond, provided that where Y is —C=, X is N; and

Z is —CH=CH—, —$(CH_2)_2$— or absent;

or a pharmaceutically acceptable salt thereof.

According to one preferred embodiment of the invention, W is N and Y is a direct bond. In another preferred embodiment, W is C and Y is —C= or —N=.

According to another preferred embodiment of the invention, Z is —CH=CH— or —$(CH_2)_2$—. In another preferred embodiment, $R_5$ and $R_6$ are each $(C_1-C_8)$alkoxy, preferably —$OCH_3$, or together are —$OCH_2O$—. Preferably $R_3$ is H. In a preferred embodiment, one or both of $R_1$ and $R_2$ is $(C_1-C_8)$alkoxy, preferably —$OCH_3$, or together are —$OCH_2O$—. In another prefered embodiment $R_2$ and $R_3$ together are —$OCH_2O$—.

Preferably, when X is C, $R_7$ is H, methyl, or ethyl; or when X is C, $R_7$ is H. Preferably, when X is N, $R_7$ is absent or $CH_3$. Similarly, it is preferred that when Y is —C=, $R_4$ is H; and when Y is —N=, $R_4$ is absent or $CH_3$. It will be understood that when X or Y is substituted N, the N will have a positive charge.

A preferred group of compounds of formula I are compounds of formula II:

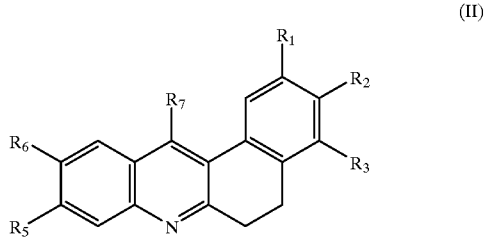

(II)

wherein $R_1$, $R_2$, $R_3$, $R_5$, $R_6$, and $R_7$ have any of the values or preferred values defined herein for a compound of formula I; or a pharmaceutically acceptable salt thereof.

The compounds of formula (I) have been shown to be effective cytotoxic agents against cancer cells, including drug-resistant cancer cells. Additionally, certain compounds of formula I show inhibitory activity against topoisomerase I. Accordingly, the invention also provides a method of inhibiting cancer cell growth in vitro, or in vivo, comprising administering to a mammal afflicted with cancer an amount of a compound of formula (I), effective to inhibit the growth of said cancer cells. According to the invention, the compound or its salt may be administered in combination with a pharmaceutically acceptable carrier.

The invention also provides pharmaceutical compositions comprising a compound of the invention in combination with a pharmaceutically acceptable carrier, as well as processes for preparing compounds of the invention, and novel intermediates useful for the synthesis of compounds of the invention.

DETAILED DESCRIPTION

According to the invention, cancer cells are inhibited in vitro or in vivo, by administration to a mammal afflicted with cancer of an effective amount of the compounds of formula (I). As used herein, an "effective amount" is that amount which results in an inhibition of growth of the target cancer cells. As described herein, a suitable dose will be in the range of about 0.5 to about 100 mg/kg of body weight per day.

The compounds and compositions described herein are believed to be effective in the treatment of solid mammalian tumors or hematologic malignancies. These solid tumors include cancers of the head and neck, lung, mesothelioma, mediastinum, esophagus, stomach, pancreas, hepatobiliary system, small intestine, colon, rectum, anus, kidney, ureter, bladder, prostate, urethra, penis, testis, gynecological organs, ovarian, breast, endocrine system, skin central nervous system; sarcomas of the soft tissue and bone; and melanoma of cutaneous and intraocular origin. Hematological malignancies include childhood leukemia and lymphomas, Hodgkin's disease, lymphomas of lymphocytic and cutaneous origin, acute and chronic leukemia, plasma cell neoplasm and cancers associated with AIDS. The preferred mammalian species for treatment are humans and domesticated animals.

Figure 1:
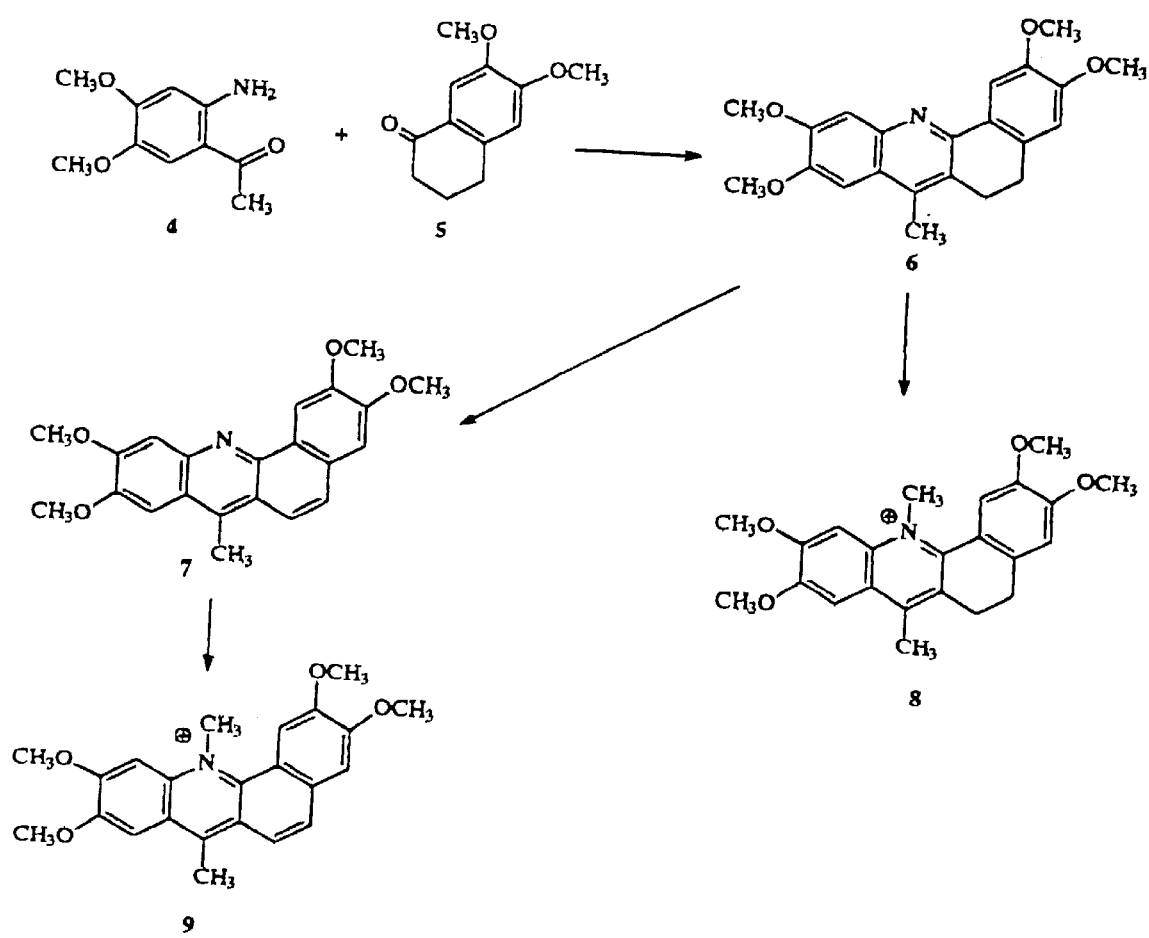
FIG. 1 illustrates the synthesis of representative benz[c] acridines of formula I.

Benz[c]acridines of formula I (X is N and Y is —C=), may conveniently be prepared by the route illustrated in FIG. 1. Reaction of 2-amino-4,5-dimethoxyacetophenone, 4, with 6,7-dimethoxy-1-tetralone, 5, provided 5,6-dihydro-2,3,9,10-tetramethoxybenz[c]acridine, 6, which, when heated as a suspension in decalin at 190° C. in the presence of Pd/C, could be converted to 2,3,9,10-tetramethoxybenz [c]acridine, 7. Both 6 and 7 could be converted to their 12-methyl derivatives by reaction with dimethyl sulfate to form the quaternary ammonium salts, 8 and 9, respectively.

Figure 2:
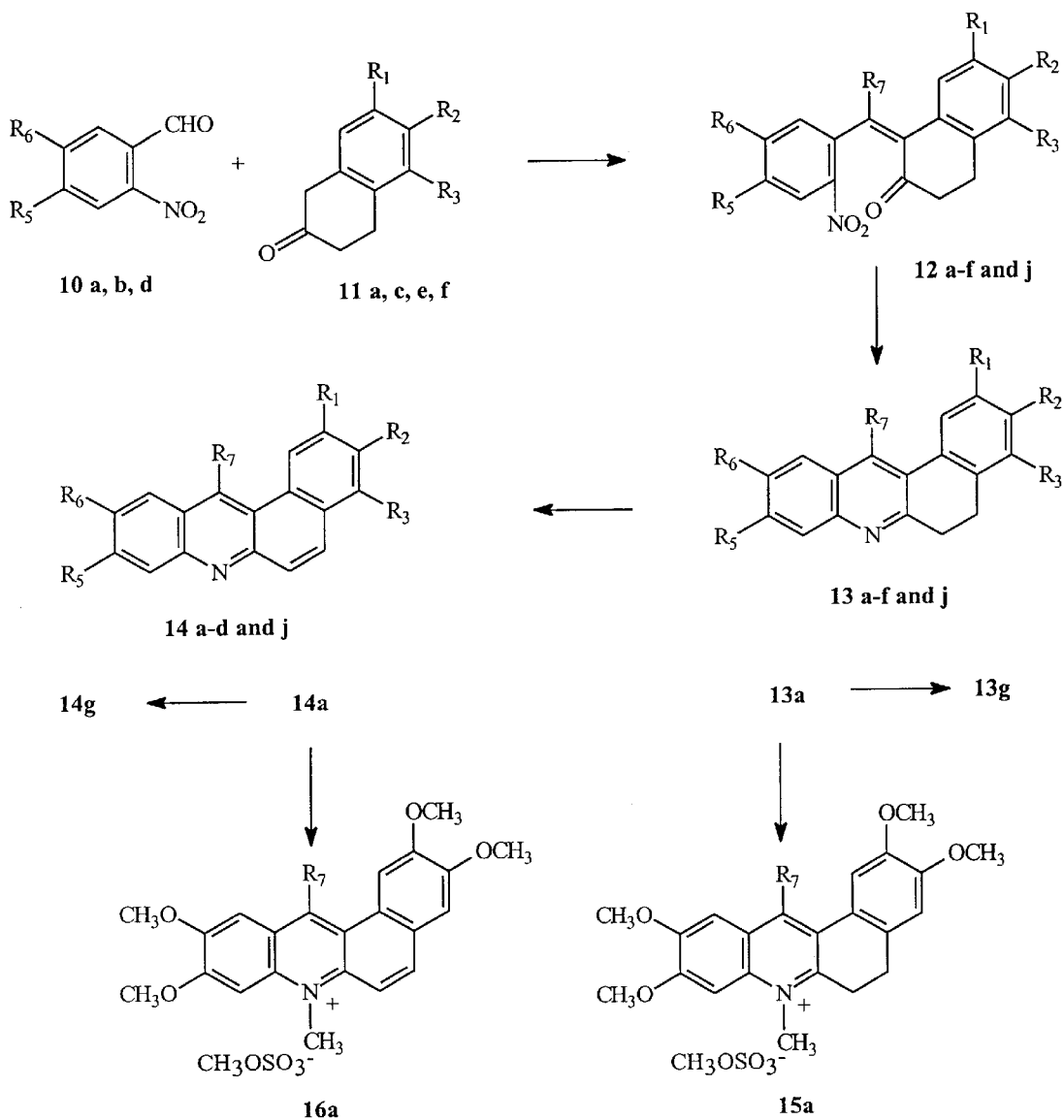
FIG. 2 illustrates the synthesis of representative benz[a] acridines of formula I.

Benz[a]acridine analogs (X is C and Y is —N=) may conveniently be prepared using procedures similar to those illustrated in FIG. 2. Knoevenagel condensation of the appropriate o-nitrobenzaldehyde with 5,6- or 6,7-disubstituted β-tetralones, provided the 1-(2'-nitrobenzylidene)-2-tetralones, 12a–f and j. Reduction with zinc in acetic acid gave the desired 5,6-dihydrobenz[a] acridine derivatives, 13a–f and j. Heating in decalin at 190° C. in the presence of Pd/C resulted in conversion of these dihydro compounds to their benz[a]acridine derivatives, 14a–d and j. Treatment of either 13a or 14a with BBr$_3$ in methylene chloride provided the tetrahydroxy analogs, 13g and 14g, respectively. Reaction of 13a or 14a with dimethyl sulfate resulted in the formation of their 7-methyl derivatives, 15a and 16a.

The starting materials, 2-nitro-4,5-dimethoxybenzaldehyde and 2-nitro-4,5-methylenedioxybenzaldehyde are commercially available. The preparation of 6-chloro-β-tetralone can be performed as described by Rosowsky, et al., J. Org. Chem. 1968, 33, 4288–4290.

Figure 3:
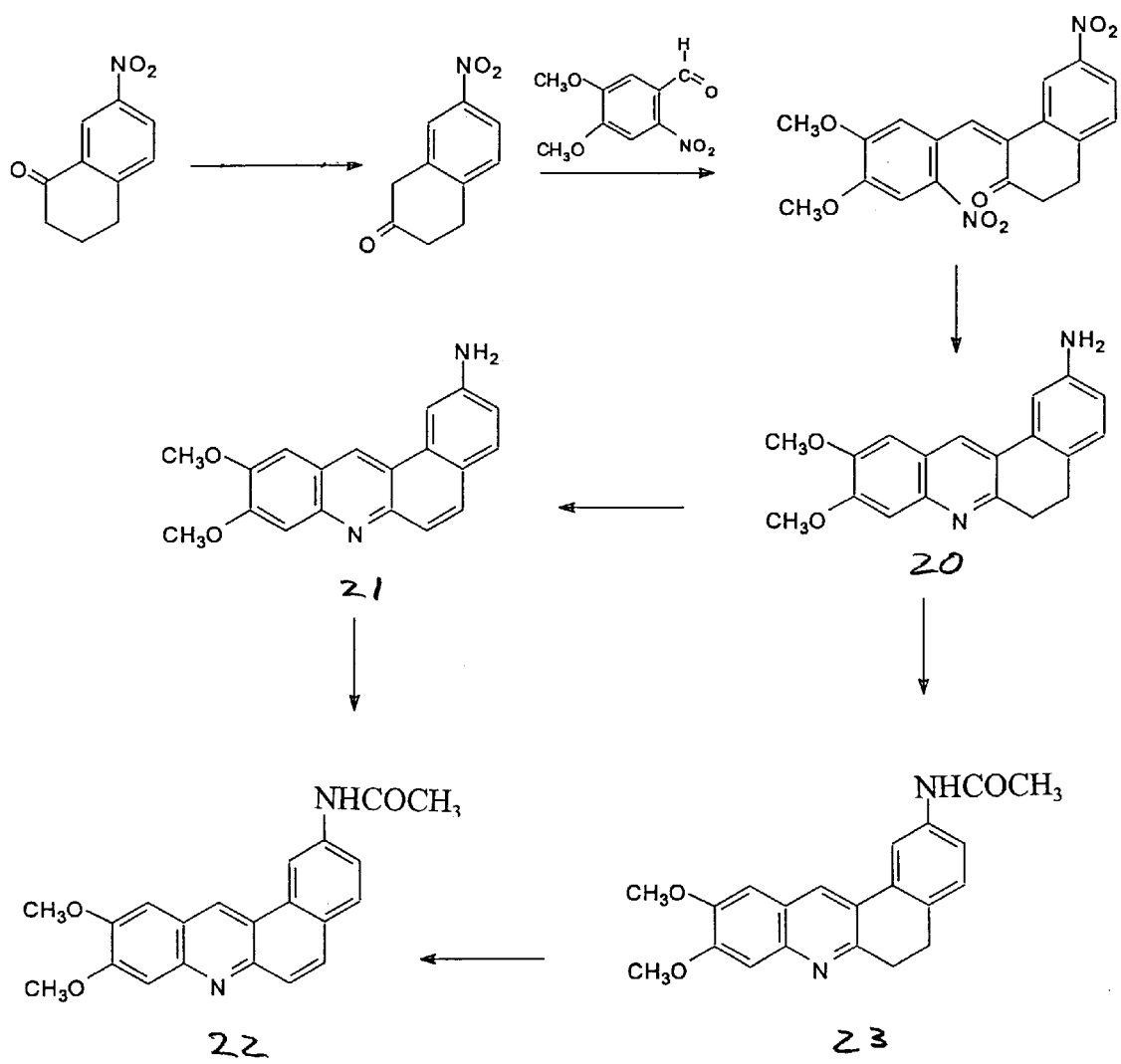
FIG. 3 illustrates the synthesis of representative compounds of the invention.

7-Nitro-β-tetralone was prepared from 7-nitro-α-tetralone, using a similar procedure to that reported by Nichols et al. (Organic Preparations and Procedures 1977, 277–280) as illustrated in FIG. 3. 7-Nitro-β-tetralone served as an intermediate in the preparation of 20, 21, 22, and 23, as illustrated in FIG. 3.

Figure 4:
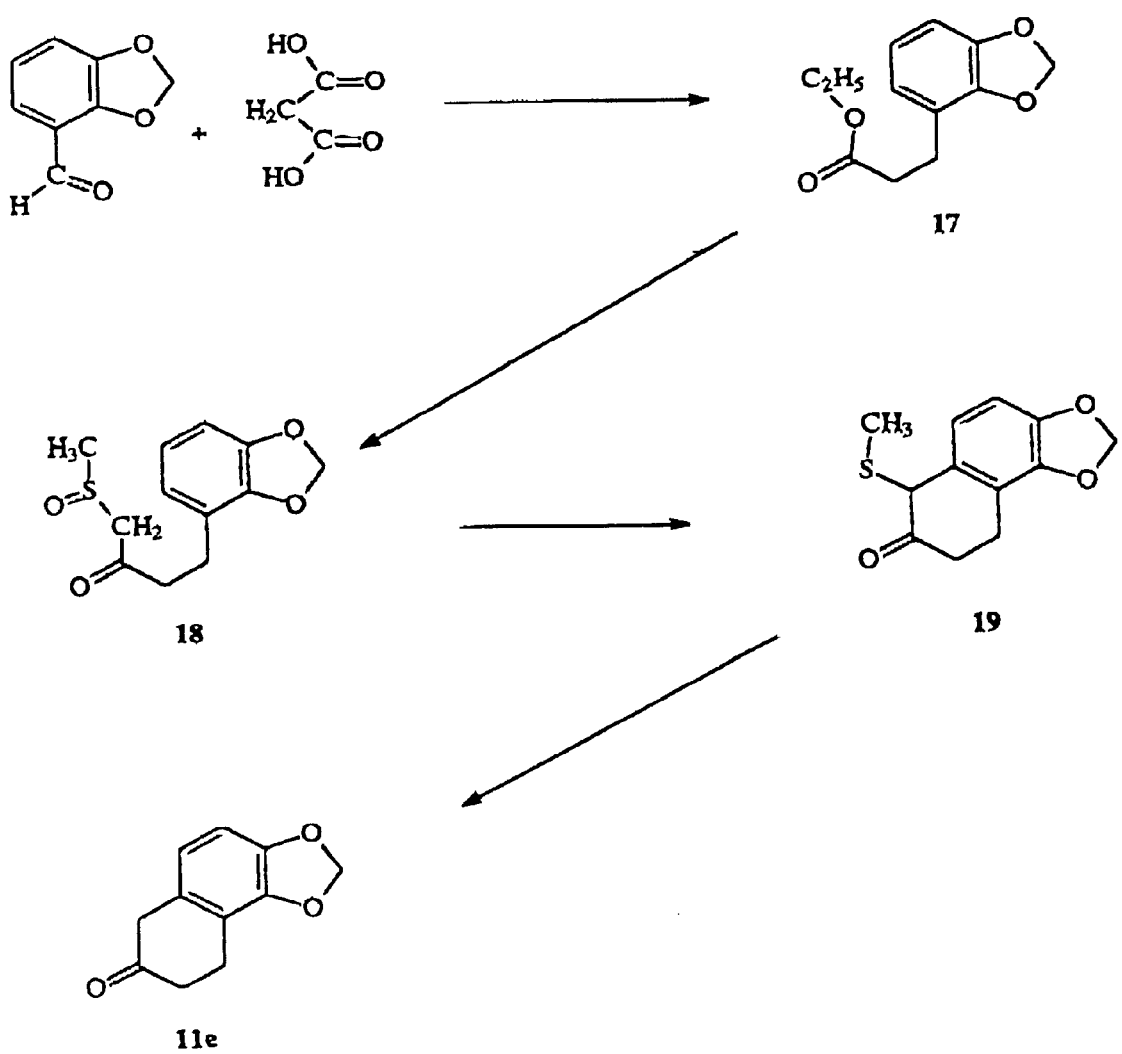
FIG. 4 illustrates the synthesis of intermediates useful for preparing compounds of formula I.

5,6-Methylenedioxy-2-tetralone (11e) was used as the requisite intermediate for the preparation of 5,6-dihydro-9, 10-dimethoxy-3,4-methylendioxybenz[a]acridine, 13e. This tetralone was prepared in six steps as illustrated in FIG. 4. 2,3-Methylenedioxybenzaldehyde was condensed with malonic acid to give 2,3-methylenedioxycinnamic acid (J. Koo et al. Org Synthesis Coll Vol. IV, 1963, 327–329). 2,3-Methylenedioxycinnamic acid was hydrogenated using 10% Pd/C to give the dihydrocinnamic acid derivative, which was then transformed into its ethyl ester, 17 (M. A. Brook; T. N. Chan, Synthesis Comm., 1983, 201–203). Ethyl-2,3-methylenedioxydihydrocinnamate was then converted to its β-ketosulfoxide, 18 (J. G. Cannon et al. J. Med. Chem., 1977, 20, 1111–1116). The β-ketosulfoxide derivative, 18, when subjected to Pummerer rearrangement by treatment with trifluoroacetic acid yielded 1,2,3,4-tetrahydro-1-methylthio-5,6-methylenedioxy-2(1H)-napthalenone, 19 (Y. Oikawk, Tetrahedron, 1974, 30, 2653–2660). Hydrogenolysis of 19 using 10% Pd/C in glacial acetic acid gave 11e (D. E. Nicholes, J. Med. Chem., 1990, 33, 703–710).

Pharmaceutically acceptable salts of compounds of formula I may be used as well in practicing the claimed methods. Pharmaceutically acceptable salts may be formed using organic or inorganic bases, such as NaOH, $Na(CO_3)_2$, $NaHCO_3$, KOH and the like; as well as acids such as hydrochloric and sulfoacetic acids and the like.

Although the compounds described herein and/or their salts may be administered as the pure chemicals, it is preferable to present the active ingredient as a pharmaceutical composition. The invention thus further provides the use of a pharmaceutical composition comprising one or more compounds and/or a pharmaceutically acceptable salt thereof, together with one or more pharmaceutically acceptable carriers and, optionally, other therapeutic and/or prophylactic ingredients. The carrier(s) must be 'acceptable' in the sense of being compatible with the other ingredients of the composition and not deleterious to the recipient thereof.

Pharmaceutical compositions include those suitable for oral or parenteral (including intramuscular, subcutaneous and intravenous) administration. The compositions may, where appropriate, be conveniently presented in discrete unit dosage forms and may be prepared by any of the methods well known in the art of pharmacy. Such methods include the step of bringing into association the active compound with liquid carriers, solid matrices, semi-solid carriers, finely divided solid carriers or combination thereof, and then, if necessary, shaping the product into the desired delivery system.

Pharmaceutical compositions suitable for oral administration may be presented as discrete unit dosage forms such as hard or soft gelatin capsules, cachets or tablets each containing a predetermined amount of the active ingredient; as a powder or as granules; as a solution, a suspension or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art., e.g., with enteric coatings.

Oral liquid preparations may be in the form of, for example, aqueous or oily suspension, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservative.

The compounds may also be formulated for parenteral administration (e.g., by injection, for example, bolus injection or continuous infusion) and may be presented in unit dose form in ampules, pre-filled syringes, small bolus infusion containers or in multi-does containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g., sterile, pyrogen-free water, before use.

For topical administration to the epidermis, the compounds may be formulated as ointments, creams or lotions, or as the active ingredient of a transdermal patch. Suitable transdermal delivery systems are disclosed, for example, in Fisher et al. (U.S. Pat. No. 4,788,603) or Bawas et al. (U.S. Pat. Nos. 4,931,279, 4,668,504 and 4,713,224). Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The active ingredient can also be delivered via iontophoresis, e.g., as disclosed in U.S. Pat. Nos. 4,140,122, 4,383,529, or 4,051,842.

Compositions suitable for topical administration in the mouth include unit dosage forms such as lozenges comprising active ingredient in a flavored base, usually sucrose and acacia or tragacanth; pastilles comprising the active ingredient in an inert base such as gelatin and glycerin or sucrose and acacia; mucoadherent gels, and mouthwashes comprising the active ingredient in a suitable liquid carrier.

When desired, the above-described compositions can be adapted to provide sustained release of the active ingredient employed, e.g., by combination thereof with certain hydrophilic polymer matrices, e.g., comprising natural gels, synthetic polymer gels or mixtures thereof.

The pharmaceutical compositions according to the invention may also contain other adjuvants such as flavorings, coloring, antimicrobial agents, or preservatives.

It will be further appreciated that the amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 $\mu$M, preferably, about 1 to 50 $\mu$M, most preferably, about 2 to about 30 $\mu$M. This may be achieved, for example, by the intravenous injection of a 0.05 to 5% solution of the active ingredient, optionally in saline, or orally administered as a bolus containing about 1–100 mg of the active ingredient. Desirable blood levels may be maintained by continuous infusion to provide about 0.01–5.0 mg/kg/hr or by intermittent infusions containing about 0.4–15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The following examples are intended to illustrate but not limit the invention.

EXAMPLES

Example I

General

Melting points were determnined with a Thomas-Hoover unimelt capillary melting point apparatus. Infrared spectral data (IR) were obtained on a Perkin-Elmer 1600 Fourier transform spectrophotometer and are reported in cm$^{-1}$. Proton ($^1$H NMR) and carbon ($^{13}$C NMR) nuclear magnetic resonance were recorded on a Varian Gemini-200 Fourier Transform spectrometer. NMR spectra (200 MHz $^1$H and 50

MHz $^{13}$C) were recorded in CDCl$_3$ (unless otherwise noted) with chemical shifts reported in δ units downfield from tetramethylsilane (TMS). Coupling constants are reported in hertz. Mass spectra were obtained from Washington University Resource for Biomedical and Bio-Organic Mass Spectrometry. Column chromatography refers to flash chromatography conducted on SiliTech 32–63 μm, (ICN Biomedicals, Eschwegge, Ger.) using the solvent systems indicated. Combustion analyses were performed by Atlantic Microlabs, Inc., Norcross, Ga., and were within ±0.4%.

2,3,9,10-Tetramethoxy-7-methyl-5,6-dihydrobenz[c] acridine (6). 2-Amino-4,5-dimethoxyacetophenone (1.0 gm, 5.1 mmol) was dissolved in 10 mL CH$_2$Cl$_2$ and hydrogen chloride (1.0 M solution, anhydrous in ether) were added with vigorous stirring at room temperature. The hydrochloride salt of the aminoacetophenone precipitated out. The solvent was removed in vacuo and the solid residue obtained dried for an hour under vacuum. The dry hydrochloride salt was then triturated with 6,7-dimethoxy-1-tetralone (1.59 gm, 7.68 mmol) and the mixture was then transferred into a sealed tube and heated at 140 °C. for 1 hour. The resulting fused plug was then dissolved in boiling methanol (300 mL). This solution was then concentrated to 200 mL and left overnight providing needle-shaped crystals. These crystals were filtered and washed with three 5 mL portions of acetone, and dried to give golden yellow needles of the benz[c]acridine hydrochloride derivative in 99% yield. The hydrochloride salt was dissolved in 200 mL boiling methanol. After the solution had cooled to room temperature concentrated NH$_4$OH was added dropwise until pH 10 was obtained. Light yellow crystals were began to form. The suspension was then diluted with 200 mL water and extracted with thrice with 100 mL portions of CH$_2$Cl$_2$. The combined extracts were washed once with 50 mL brine, dried using anhydrous Na$_2$SO$_4$, filtered, and the solvent removed in vacuo to give the free base; mp 240° C.; IR (Nujol): 2922, 1620; $^1$H NMR: δ2.52 (3H, s), 2.86 (2H s), 3.02 (2H, t), 3.90 (3H, s), 3.98 (3H, s), 4.03 (3H, s), 4.05 (3H, s), 6.70 (1H, s), 7.08 (1H, s), 7.43 (1H, s), 8.04 (1H, s); $^{13}$C NMR: δ16.5, 25.4, 28.0, 56.6, 56.7, 57.8, 58.3, 102.3, 102.7, 110.9, 111.8, 119.5, 123.2, 127.7, 134.7, 135.6, 146.3, 148.5, 149.7, 151.3, 153.5, 155.2; HRMS calcd for C$_{22}$H$_{23}$NO$_4$: 365.1630; found: 365.1628.

5,6-Methylenedioxy-2-tetralone (11e): 0.669 g (2.83 mM) of 19 was taken up in 10 mL glacial acetic acid in a hydrogenation flask. 0.46 g of 10% Pd-C was added and this mixture was shaken in a Parr apparatus at 40 psig of hydrogen for 40 hours. The reaction mixture was filtered through a celite bed, which was washed thrice with 5 mL portions of glacial acetic acid. The glacial acetic acid was rotaevaporated to give the crude tetralone, 11e. The crude tetralone was then treated with sodium bisulfite to convert it to the more stable bisulfite adduct. Pure tetralone was generated as required from its bisulfite adduct by treatment with 10% sodium carbonate solution followed by extraction with dichloromethane; mp=90–91° C., (lit$^{36}$ 88–91° C.), IR (Nujol) 1715; $^1$H NMR: δ2.50 (2H, t), 2.98 (2H, t), 3.50 (2H, s), 5.93 (2H, s), 6.56 (1H, d, J=6), 6.65 (1H, d, J=6); $^{13}$C NMR: δ21.6, 37.9, 45.0, 101.5, 107.4, 118.5, 121.1, 127.8, 144.1, 146.2, 211.2; Anal. (C$_{11}$H$_{10}$O$_3$) C, H.

Example II
General Procedure for the Synthesis of 1-(2'-nitrobenzylidene)-2-tetralone derivatives (FIG. 2)

A glacial acetic acid (10 mL) solution of 2.45 mmol of the respective 2-tetralone, 2-nitrobenaldehyde, and sodium acetate was refluxed for 3–8 h under nitrogen atmosphere. The reaction mixture was then allowed to cool to room temperature. The mixture was the carefully loaded on a silica gel (75 gm) column and chromatographed using a 1:1 mixture of ethyl ether and hexanes. The yellow colored compound generally eluting fourth from the column was collected to give the respective tetralone derivatives in 20–25% yield.

1-(2'-Nitro-4',5'-dimethoxybenzylidene)-6,7-dimethoxy-2-tetralone (12a). Prepared from 6,7-Dimethoxy-2-tetralone and 6-nitroveratraldehyde; mp 65–66° C.; IR (Nujol): 2855, 1720, 1540; $^1$H NMR: δ2.71 (2H, t), 2.98 (2H t), 3.35 (3H, s), 3.66 (3H, s), 3.89 (3H, s), 3.97 (3H,s), 6.41 (1H, s), 6.62 (1H, s), 6.73 (1H, s), 7.74 (1H, s), 7.91 (1H, s); $^{13}$C NMR: δ28.4, 39.7, 56.5, 56.6, 56.8, 56.9, 107.7, 108.6, 111.2, 113.1, 128.1, 129.3, 130.3, 132.2, 133.3, 148.9, 149.0, 150.0, 153.3, 200.7.

1-(2'-Nitro-4',5'-methylenedioxybenzylidene)-6,7-dimethoxy-2-tetralone (12b). Prepared from 6,7-dimethoxy-2-tetralone and 6-nitropiperonal; mp 76–77° C.; IR (Nujol): 2875,1723, 1553; $^1$H NMR: δ2.68 (2H, t), 3.00 (2H t), 3.41 (3H, s), 3.90 (3H, s), 6.08 (2H, s), 6.37 (1H, s), 6.51 (1H, s), 6.73 (1H, s), 7.68 (1H, s), 7.83 (1H, s); $^{13}$C NMR: δ28.0, 38.0, 56.1, 56.4, 103.7, 105.9, 110.1, 111.3, 112.6, 124.3, 130.8, 131.1, 132.2, 133.8, 147.6, 148.4, 149.7, 152.5.

1-(2'-Nitro-4',5'-dimethoxybenzylidene)-2-tetralone (12c). Prepared from 2-tetralone and 2-nitro-4,5-dimethoxybenzaldehyde; mp 58–60° C.; IR (Nujol): 1724, 1540; $^1$H NMR: δ2.71 (2H, t), 3.08 (2H t), 3.56 (3H, s), 4.02 (3H, s), 6.51 (1H, s), 6.92–6.96 (2H, m), 7.17–7.24 (2H, m), 7.73 (1H, s), 8.00 (1H, s); $^{13}$C NMR: δ28.3, 27.8, 56.7, 56.9, 108.3, 112.5, 126.7, 127.6, 128.5, 128.8, 129.9, 132.3, 133.4, 134.5, 138.8, 141.6, 149.4, 153.5.

1-(2'-Nitro-benzylidene)-6,7-dimethoxy-2-tetralone (12d). Prepared from 6,7-dimethoxy-2-tetralone and 2-nitrobenzaldehyde; mp 63–64° C.; IR (Nujol): 1712, 1540; $^1$H NMR: δ2.69 (2H, t), 3.01 (2H t), 3.25 (3H, s), 3.88 (3H, s), 6.26 (1H, s), 6.72 (1H, s), 7.25–7.26 (1H, m), 7.44–7.50 (2H, m), 7.87 (1H, s), 8.12–8.17 (1H, m); $^{13}$C NMR: δ28.0, 37.9, 55.7, 56.3, 108.6, 111.3, 112.5, 124.2, 124.9, 125.4, 129.3, 130.1, 131.8, 133.5, 133.9, 134.7, 147.5, 149.6, 200.7.

1-(2'-Nitro-4',5'-dimethoxybenzylidene)-5,6-methylenedioxy-2-tetralone (12e). Prepared from 5,6-methylendioxy-2-tetralone and 2-nitro-4,5-dimethoxybenzaldehyde; mp 66–68° C.: IR (Nujol): 1710, 1553; $^1$H NMR: δ2.98 (2H, t), 3.19 (2H, t), 4.02 (3H, s), 4.03 (3H, s), 6.03 (2H, s), 6.82 (1H, d, J=8.1), 7.07 (1H, s), 7.29 (1H, d, J=8.1), 7.49 (1H, s), 8.20 (1H, s); $^{13}$C NMR: δ21.8, 30.8, 56.5, 56.7, 101.8, 105.7, 107.6, 117.9, 119.1, 123.9, 125.9, 126.9, 128.7, 143.4, 145.4, 147.7, 150.1, 152.9, 156.1, 176.4; Anal. (C$_{20}$H$_{17}$NO$_7$) C, H, N.

1-(2'Nitro-4',5'-dimethoxybenzylidene)-5,6-dimethoxy-2-tetralone (12f). Prepared from 5,6-dimethoxy-2-tetralone and 2-nitro-4,5-dimethoxybenzaldehyde; mp 70–72° C.; IR (Nujol): 1715, 1550; $^1$H NMR: δ2.59 (2H, t), 3.06 (2H, t), 3.78 (3H, s), 3.86 (3H, s), 3.88 (3H, s), 3.92 (3H, s), 6.47 (1H, s), 6.77 (1H, d, J=8.2), 7.41 (1H, d, J=8.2), 7.67 (1H, s); $^{13}$C NMR: δ19.7, 32.0, 56.3, 56.7, 56.8, 56.85, 108.1, 121.9, 125.6, 126.1, 128.0, 129.2, 132.1, 132.9, 133.7, 140.3, 141.4, 149.3, 152.9, 153.5, 200.9; Anal. (C$_{21}$H$_{21}$NO$_7$) C, H, N.

1-(2'-Nitro-4',5'-dimethoxybenzylidene)-6-chloro-2-tetralone (12j). Prepared from 6-chloro-2-tetralone and 2-nitro-4,5-dimethoxybenzaldehyde; mp 56–58° C.; IR (Nujol): 2922, 1730, 1100; $^1$H NMR: δ2.68 (2H, t), 3.05 (2H t), 3.62 (3H, s), 3.98 (3H, s), 6.48 (1H, s), 6.82 (1H, d, J=8.4), 6.90–6.96 (1H, dd, J=8.4, 2.1), 7.26 (1H, d, J=2.1), 7.74 (1H, s), 8.01 (1H, s); $^{13}$C NMR: δ28.2, 37.4, 56.8, 56.9, 108.3, 112.2, 127.0, 127.2, 128.6, 130.9, 131.1, 133.3, 134.2, 134.5, 140.5, 141.5, 149.6, 153.7.

1-(2'-Nitro-4',5'-dimethoxybenzylidene)-7-nitro-2-tetralone (FIG. 3). Prepared from 7-nitro-2-tetralone and 2-nitro-4,5-dimethoxybenzaldehyde; mp 125° C.; IR (Nujol): 1724, 1540, 1545; $^1$H NMR: δ2.69 (2H, t), 3.16 (2H t), 3.59 (3H, s), 4.01 (3H, s), 6.45 (1H, s), 7.41 (1H, d, J=8.1), 7.68 (1H, d, J=2.2), 7.72 (1H, s), 7.94–7.99 (1H, dd, J=8.4, 2.2), 8.08 (1H, s); $^{13}$C NMR: δ28.4, 36.9, 56.9, 57.0, 108.7, 111.6, 123.2, 124.2, 126.1, 129.7, 132.5, 133.9, 135.8, 141.4, 145.8, 146.8, 150.1, 154.1, 198.4.

Example III

General Procedure for the Synthesis of 5, 6-dihydrobenz[a] acridine Derivatives (FIG. 2)

The respective 1-(2'-nitrobenzylidene)-2-tetralone derivative (0.3 mmol) was dissolved in 10 mL glacial acetic acid and refluxed with zinc dust (1.64 mmol) under a nitrogen atmosphere for 1–4 h. The reaction mixture was allowed to cool to room temperature and then the entire mixture was loaded carefully on silica gel (100 gm) column and chromatographed first with 500 mL of ethyl ether to remove acetic acid followed by elution with hexanes/ethyl acetate. The polarity of the mobile phase was reduced, if necessary, by mixing suitable proportions of hexanes. The relevant fractions were pooled and concentrated in vacuo to yield 83–95% of corresponding 5,6-dihydrobenz[a]acridines.

2,3,9,10-Tetramethoxy-5,6-dihydrobenz[a]acridine (13*a*). Prepared from 1-(2'-Nitro-4',5'-dimethoxybenzylidene)-6,7-dimethoxy-2-tetralone; mp 182–183° C.; IR (Nujol): 3210, 1615; $^1$H NMR: δ2.99 (2H, t), 3.23 (2H t), 3.94 (3H, s), 4.00 (3H, s), 4.02 (3H, s), 4.04 (3H,s), 6.79 (1H, s), 7.10 (1H, s), 7.31 (1H, s), 7.54 (1H, s), 8.17 (1H, s); $^{13}$C NMR: δ28.8, 32.3, 56.5, 56.7, 105.7, 107.2, 107.5, 111.8, 123.9, 125.8, 127.1, 128.0, 130.5, 143.1, 148.8, 149.6, 152.8, 156.7, 176.7; HRMS calcd for $C_{21}H_{21}NO_4$: 351.1471; found: 351.1475.

2,3,-Dimethoxy-9,10-methylenedioxy-5,6-dihydrobenz[a]acridine (13*b*). Prepared from 1-(2'-Nitro-4',5'-methylenedioxybenzylidene)-6,7-dimethoxy-2-tetralone; mp 218–219° C.; IR (Nujol): 2780,1630; $^1$H NMR: δ2.97 (2H, t), 3.17 (2H t), 3.93 (3H, s), 4.00 (3H, s), 6.07 (2H, s), 6.79 (1H, s), 7.07 (1H, s), 7.29 (1H, s), 7.32 (1H, s), 8.07 (1H, s); $^{13}$C NMR: δ29.0, 33.1, 56.5, 56.7, 102.1, 103.3, 105.7, 107.6, 111.8, 125.2, 125.9, 127.0, 128.0, 130.6, 145.0, 147.9, 148.8, 149.6, 150.8, 156.9; HRMS calcd for $C_{20}H_{17}NO_4$: 335.1158; found: 335.1162.

9,10-Dimethoxy-5,6-dihydrobenz[a]acridine (13*c*). Prepared from 1-(2'-Nitro-4', 5'-dimethoxybenzlidene)-2-tetralone; mp 95–96° C.; IR (Nujol): 1633, 1516; $^1$H NMR: δ3.06 (2H, t), 3.24 (2H t), 4.02 (3H, s), 4.03 (3H, s), 7.10 (1H, s), 7.28–7.37 (3H, m), 7.50 (1H, s), 7.82 (1H, d, J=7.0), 8.29 (1H, s); $^{13}$C NMR: δ29.2, 32.3, 56.5, 56.7, 105.9, 107.4, 124.0, 124.3, 127.3, 127.7, 128.5, 128.9, 129.1, 133.8, 137.6, 144.2, 150.5, 153.1; HRMS calcd for $C_{19}H_{17}NO_2$: 291.1259; found: 291.1250.

2,3-Dimethoxy-5,6-dihydrobenz[a]acridine (13*d*). Prepared from 1-(2'-Nitro-benzylidene)-6,7-dimethoxy-2-tetralone; mp 55–56° C.; IR (Nujol): 2815, 1615; $^1$H NMR: δ2.96 (2H, t), 3.23 (2H t), 3.90 (3H, s), 3.98 (3H, s), 6.75 (1H, s), 7.30 (1H, s), 7.44 (1H, t), 7.60 (1H, t), 7.80 (1H, d, J=10.2), 8.0 (1H, d, J=10.2), 8.19 (1H, s); $^{13}$C NMR: δ27.3, 28.9, 56.5, 56.6, 106.2, 110.7, 125.2, 125.5, 127.6, 127.8, 131.2, 132.4, 133.7, 133.9, 134.2, 136.3, 151.3, 153.6, 157.8; HRMS calcd for $C_{19}H_{17}NO_2$: 291.1259; found: 291.1246.

5,6-Dihydro-9,10-dimethoxy-3,4-methylenedioxybenz[a]acridine (13*e*). Prepared from 1-(2'-nitro-4',5'-dimethoxybenzylidine)-5,6-methylenedioxy-2-tetralone; mp 220–222° C.; IR (Nujol): 1715, 1532; $^1$H NMR: δ3.02 (2H, t), 3.19 (2H, t), 4.02 (3H, s), 4.03 (3H, s), 6.03 (2H, s), 6.83 (1H, d, J=8.1), 7.07 (1H, s), 7.34–7.38 (2H, m), 8.19 (1H, s); $^{13}$C NMR: δ30.2, 32.3, 56.5, 56.6, 101.8, 105.8, 107.5, 107.8, 117.9, 119.2, 123.8, 126.9, 128.3, 128.7, 143.2, 145.4, 147.6, 149.9, 152.7, 156.3; Anal. ($C_{20}H_{17}NO_4$) C, H, N.

5,6-Dihydro-3,4,9,10-tetramethoxybenz[a]acridine (13*f*). Prepared from 1-(2'-nitro-4',5'-dimethoxybenzylidine)-5,6-dimethoxy-2-tetralone; mp 195–196° C.; IR (Nujol): 1730, 1515; $^1$H NMR: δ2.82 (2H, t), 3.20 (2H, t), 3.86 (3H, s), 3.91 (3H, s), 4.03 (3H, s), 4.04 (3H, s), 6.93 (1H, d, J=8.6), 7.10 (1H, s), 7.52 (1H, s), 7.56 (1H, d, J=8.6), 8.27 (1H, s); $^{13}$C NMR: δ21.8, 31.6, 56.4, 56.6, 56.8, 61.1, 105.8, 106.4, 106.5, 107.6, 111.4, 111.9, 120.4, 124.1, 127.1, 129.3, 131.6, 150.3, 150.4, 153.4, 156.3. Anal. ($C_{21}H_{21}NO_4$) C, H, N.

2-Amino-9,10-dimethoxy-5,6-dihydrobenz[a]acridine (FIG. 3, 20). Prepared from 1-(2'-Nitro-4',5'-dimethoxybenzylidine)-7-nitro-2-tetralone; mp 185° C.; IR (Nujol): 3345, 2895, 1330; $^1$H NMR (CD$_3$OD): δ2.96 (2H, t), 3.36 (2H t), 3.98 (3H, s), 4.02 (3H, s), 7.24 (1H, d, J=10.0), 7.32–7.38 (2H, m), 7.88 (1H, s), 8.17 (2H, s); $^{13}$C NMR (CD$_3$OD): δ24.5, 27.7, 57.0, 57.1, 99.4, 107.9, 117.1, 121.9, 123.2, 125.9, 128.9, 130.1, 133.2; HRMS calcd for $C_{19}H_{18}N_2O_2$: 306.1369; found: 306.1369.

3-Chloro-9,10-dimethoxy-5,6-dihydrobenz[a]acridine (13*j*). Prepared from 1-(2'-Nitro-4',5'-dimethoxybenzylidene)-6-chloro-2-tetralone; mp 197° C.; IR (Nujol): 2895, 1105; $^1$H NMR: δ2.96 (2H, t), 3.12 (2H t), 3.97 (3H, s), 3.98 (3H, s), 7.00 (1H, s), 7.20–7.26 (2H, m), 7.32 (1H, s), 7.64 (1H, d, J=8.1), 8.11 (1H, s); $^{13}$C NMR: δ29.1, 32.6, 56.5, 56.6, 105.8, 107.8, 123.6, 125.6, 125.8, 127.7, 128.6, 128.8, 132.3, 133.9, 139.3, 144.4, 150.0, 153.0, 156.6; HRMS calcd for $C_{19}H_{16}ClNO_2$: 325.0869; found: 325.0887.

Example IV

General Procedure for the Synthesis of benz[a]acridines and benz[c]acridines from Their 5, 6-dihydro Derivatives (FIG. 2)

The respective 5,6-dihydrobenz[a]acridine or 5,6-dihydrobenz[c]acridine derivatives (0.22 mmol) were refluxed in 15 mL decalin with 76 mg of 10% palladium on carbon under nitrogen atmosphere for 2–9 h. The reaction mixture was then quickly filtered under suction while hot through a celite bed using a sintered glass funnel. The filter bed was washed thoroughly thrice using 20 mL portions of boiling chloroform followed by two 20 mL portions of boiling ethyl acetate. The combined filtrate was then concentrated in vacuo and dried under vacuum to give the respective benz[a]acridine derivatives.

2,3,9,10-Tetramethoxy-7-methylbenz[c]acridine (FIG. 1, 7). Prepared from 6; mp>250° C.; IR (Nujol): 3520, 1633, 1610; $^1$H NMR: δ2.87 (3H, s), 4.03 (3H, s), 4.04 (3H, s), 4.13 (3H,s), 4.23 (3H,s), 7.17 (1H, s), 7.20 (1H, s, J=9.2), 7.59 (1H, s), 7.80 (1H, d, J=9.2), 8.87 (1H, s); $^{13}$C NMR: δ14.4, 56.4, 56.7, 101.7, 106.0, 108.2, 108.3, 120.8, 122.1, 122.4, 125.5, 125.8, 126.9, 128.6, 135.7, 139.0, 145.2, 149.8, 150.9, 153.3; HRMS calcd for $C_{22}H_{21}NO_4$: 363.1470; found: 363.1472.

2,3,9,10-Tetramethoxybenz[a]acridine (14*a*). Prepared from 13*a*; mp 247–249° C.; IR (Nujol): 2810, 1630; $^1$H NMR: δ3.99 (3H, s), 4.01 (3H, s), 4.03 (3H,s), 4.08 (3H,s), 7.08 (1H, s), 7.12 (1H, s), 7.41 (1H, s), 7.74 (1H, d, J=9.3), 7.81 (2H, m), 8.82 (1H, s); $^{13}$C NMR: δ56.3, 56.4, 56.5, 56.6, 103.9, 104.8, 106.8, 109.2, 122.8, 123.0, 124.5, 126.2, 126.4, 127.7, 130.7, 145.7, 147.2, 149.8, 149.9, 150.3, 153.9; HRMS calcd for $C_{21}H_{19}NO_4$: 349.1314; found: 349.1314.

2,3,-Dimethoxy-9,10-methylenedioxybenz[a]acridine (14b). Prepared from 13b; mp 245–246° C.; IR (Nujol): 2790, 1630; $^1$H NMR: δ4.06 (3H, s), 4.16 (3H, s), 6.15 (2H, s), 7.25 (2H, s), 7.48 (1H, s), 7.84 (1H, d, J=8.2), 7.99 (1H,s), 8.99 (1H, s); $^{13}$C NMR: δ56.5, 56.6, 102.3, 102.4, 104.1, 104.9, 109.4, 112.8, 122.9, 124.4, 126.5, 126.7, 128.5, 130.9, 135.7, 147.0, 147.4, 148.4, 150.1, 152.0; HRMS calcd for $C_{20}H_{15}NO_4$: 333.1002; found: 333.1004.

9,10-Dimethoxybenz[a]acridine (14c). Prepared from 13c; mp 181–182° C.; IR (Nujol): 2883, 1621; $^1$H NMR: δ4.09 (6H, s), 7.26 (1H, s), 7.54 (1H, s), 7.60–7.71 (2H, m), 7.89–7.96 (3H, m), 8.69 (1H, d, J=8.1), 9.23 (1H, s); $^{13}$C NMR: δ56.6, 56.7, 105.1, 107.1, 122.9, 123.3, 123.4, 125.5, 127.6, 128.5, 128.7, 129.3, 130.4, 131.5, 131.6, 135.7, 146.4, 148.0, 150.6, 154.3; HRMS calcd for $C_{19}H_{17}NO_2$: 289.1104; found: 289.1104.

2,3-Dimethoxy-benz[a]acridine (14d). Prepared from 13d; mp 190–192° C.; IR (Nujol): 2881, 1632; $^1$H NMR: δ4.02 (3H, s), 4.13 (3H, s), 7.18 (1H, s), 7.51–7.59 (1H, m), 7.72–7.81 (1H, m), 7.83 (1H, s), 7.89 (1H, s), 7.93–8.22 (2H, m), 8.23 (1H, d, J=8.5), 9.13 (1H, s); $^{13}$C NMR: δ56.5, 56.6, 104.4, 109.5, 124.2, 124.5, 126.3, 126.4, 126.8, 126.9, 128.5, 129.4, 130.0, 130.1, 130.2, 132.3, 148.1, 149.2, 150.1, 150.2; HRMS calcd for $C_{19}H_{15}NO_2$: 289.1104; found: 289.1099.

3-Chloro-9,10-dimethoxybenz[a]acridine (14j). Prepared from 13j; mp 241–243° C.; IR (Nujol): 2893, 1108; $^1$H NMR: δ4.04 (3H, s), 4.06 (3H, s), 7.09 (1H, s), 7.43 (1H, s), 7.51–7.57 (1H, dd, J=8.8, 2.2), 7.68 (1H, d, J=9.1), 7.75 (1H, d, J=2.2), 7.90 (1H, d, J=9.1), 8.42 (1H, d, J=8.8), 8.92 (1H, s); $^{13}$C NMR: δ56.6, 56.7, 104.9, 106.9, 122.7, 123.3, 124.3, 127.8, 128.2, 128.3, 128.6, 129.7, 130.2, 132.5, 133.2, 146.4, 147.4, 150.7, 154.4; HRMS calcd for $C_{19}H_{14}ClNO_2$: 323.0713; found: 323.0713.

Example V

General Procedure for N-methylation of benz[a]acridines and benz[c]acridines

Dimethyl sulfate (4 mL) was added to 0.27 mmol of the respective benz[a]acridine or benz[c]acridine and the mixture heated under nitrogen atmosphere in an oil bath at 150° C. for 20 min–5 hours. Anhydrous ethyl ether (10 mL) was added to the reaction mixture with vigorous stirring after it had cooled to room temperature. The precipitated quaternary salt was filter under suction and washed thrice with 10 mL portions of anhydrous ethyl ether and dried. The quaternary salts were crystallized from boiling methanol in 90% yield.

2,3,9,10-Tetramethoxy-7,1 2-dimethyl-5,6-dihydrobenz [c]acridinium methosulfate (FIG. 1, 8). Prepared from 6; mp>250° C.; IR (Nujol): 3510,1645, 1613; $^1$H NMR (CD$_3$OD): δ2.90 (3H, s), 2.96 (2H, t), 3.08 (2H, t), 3.93 (3H,s), 4.00 (3H,s), 4.10 (3H, s), 4.18 (3H,s), 4.62 (3H, s), 7.17 (1H, s), 7.42 (1H, s), 7.61 (1H, s), 7.63 (1H, s); $^{13}$C NMR: δ16.6, 27.2, 29.0, 46.2, 57.0, 57.2, 57.3, 57.4, 100.7, 105.5, 112.5, 115.2, 121.2, 125.1, 133.4, 138.5, 139.7, 149.7, 150.5, 152.7, 152.9, 154.8, 157.4; HRMS calcd for $C_{23}H_{26}NO_4+$: 380.1858; found: 380.1856.

2,3,9,10-Tetramethoxy-7,1 2-dimethylbenz [c]acridinium methosulfate (FIG. 1, 9). Prepared from 7; mp>240° C.; IR (Nujol): 3495, 1640, 1615; $^1$H NMR (DMSO-d$_6$): δ2.53 (3H, s), 3.39 (3H,s), 3.97 (3H,s), 4.03 (3H, s), 4.16 (3H,s), 4.17 (3H, s), 7.69 (1H, s), 7.75 (1H, s), 7.91 (1H, s), 7.99 (1H, d, J=9.5), 8.24 (1H, d, J=9.5); $^{13}$C NMR: δ15.5, 55.4, 56.4, 56.5, 56.6, 56.7, 102.1, 106.3, 110.3, 111.2, 125.8, 123.2, 122.5, 128.8, 129.0, 130.9, 133.3, 139.0, 141.1, 147.6, 152.1, 153.8, 155.3; HRMS calcd for $C_{23}H_{24}NO_4+$: 378.1698; found: 378.1695.

2,3,9,10-Tetramethoxy-7-methyl-5,6-dihydrobenz[a] acridinium methosulfate (15a). Prepared from 13a; mp>250° C.; IR (Nujol): 3490,1620; $^1$H NMR (DMSO-d$_6$): δ3.06 (2H, t), 3.37 (5H, t), 3.85 (3H, s), 3.93 (3H, s), 4.02 (3H, s), 4.05 (3H,s), 7.04 (1H, s), 7.45 (1H, s), 7.62(1H, s), 7.63 (1H, s), 9.29 (1H, s); $^{13}$C NMR: δ25.9, 27.8, 53.1, 56.0, 56.1, 56.7, 56.8, 99.6, 106.6, 106.7, 107.9, 112.2, 112.3, 122.0, 124.4, 127.3, 129.1, 148.8, 150.3, 151.1, 153.0, 155.3; HRMS calcd for $C_{22}H_{24}NO_4+$: 366.1706; found: 366.1706.

2,3,9,10-Tetramethoxy-7-methylbenz[a]acridinium methosulfate (16a). Prepared from 14a; mp>250° C.; IR (Nujol): 2820, 1620; $^1$H NMR (DMSO-d$_6$): μ3.39 (3H, s), 3.96 (3H, s), 3.97 (3H, s), 4.03 (3H, s), 4.07 (3H, s), 7.59 (1H, s), 7.67 (1H, s), 7.85 (1H, d, J=9.2), 8.25 (1H, s), 8.31 (1H, d, J=9.2), 8.75 (1H, s), 10.18 (1H, s); $^{13}$C NMR: δ54.4, 56.8, 56.9, 57.5, 57.9, 105.7, 106.7, 107.9, 110.4, 123.2, 125.3, 125.4, 127.8, 127.9, 128.3, 131.4, 146.8, 149.3, 152.0, 158.5, 159.9; HRMS calcd for $C_{22}H_{22}NO_4+$: 364.1549; found: 364.1542.

Example VI

General Procedure for the Synthesis of 2,3,9,10-tetrahydroxy-5,6-dihydrobenz[a]acridine (FIG. 2, 13g) and 2,3,9,10-tetrahydroxybenz[a]acridine (FIG. 2, 14g).

The respective benz[a]acridine derivatives (0.195 mmol) were dissolved in 2 mL CH$_2$Cl$_2$ and the solution was chilled to −50° C. using a cooling bath of isopropanol and dry-ice. 1.95 mmols of boron tribromide (1.0 M) solution in CH$_2$Cl$_2$ was added under a nitrogen atmosphere. The reaction mixture was stirred at −50° C. for 1 hour. and then slowly allowed to come to room temperature over a period of 4 hours. The reaction mixture was then cooled to −10° C. and was quenched by addition of 5 mL saturated ammonium chloride solution. The resulting solution was evaporated to dryness and the residue obtained was extracted thrice with 20 ml portions of boiling acetone. The resulting yellow suspensions were filtered each time. The undissolved precipitate was dissolved in 5 mL boiling methanol and set aside overnight. Needle shaped crystals of the respective tetrahydroxybenz[a]acridines were formed in 95% yield.

2,3,9,10-tetrahydroxy-5,6-dihydrobenz[a]acridine (13g). Prepared from 13a; mp>220° C.; IR (Nujol): 3361, 3164, 2719, 1620; $^1$H NMR (CD$_3$OD): δ2.97 (2H, t), 3.35 (2H t), 6.77 (1H, s), 7.45 (3H, m), 8.83(1H, s); $^{13}$C NMR (CD$_3$OD): δ27.4, 29.2, 102.9, 110.9, 112.5, 116.6, 122.9, 126.5, 128.5, 129.4, 134.8, 135.6, 146.6, 148.6, 151.1, 152.9, 156.0; HRMS calcd for $C_{17}H_{13}NO_4$: 295.0845; found: 295.0842.

2,3,9,10-tetrahydroxybenz[a]acridine (14g). Prepared from 14a; mp>270° C.; IR (KBr): 3361,3164, 1620,1516; $^1$H NMR (CD$_3$OD): δ7.26 (1H, s), 7.37 (1H, s), 7.56(1H, s), 7.61 (1H, d, J=9.2), 8.05 (2H, m), 9.61(1H, s),; $^{13}$C NMR (CD$_3$OD): δ101.1, 108.7, 110.3, 114.3, 114.7, 122.9, 124.4, 124.8, 126.7, 137.6, 137.8, 138.3, 139.0, 149.4, 150.7, 150.8, 159.3; HRMS calcd for $C_{17}H_{11}NO_4$: 293.0688; found: 293.0685.

Example VII

Synthesis of 7-nitro-2-tetralone from 7-nitro-1-tetralone (FIG. 3)

7-Nitro-1,2,3,4-tetrahydro-1-napthalenol. To a slurry of 2.88 g (15 mmol) of 7-nitro-1-tetralone in 60 mL absolute ethanol was added 0.58 g (15 mmol) of sodium borohydride. The reaction mixture was then stirred at room temperature for 2 hours. The resulting mixture was then rotaevaporated to dryness and the residue obtained was suspended in 100 mL of water. 3 N hydrochloric acid was added dropwise until the reaction mixture had pH 7. The suspension obtained was then extracted with five 50 mL portions of ethyl ether and the combined ether layer was washed once with 100 mL water. The ether layer was dried over anhydrous sodium sulfate, filtered and rotaevaporated to give an off-white residue which was recrystallized from a 1:1 mixture of absolute ethanol and water to yield 2.68 g (92%) of the napthalenol; mp 112–113° C.; IR (KBr): 3300; $^1$H NMR: δ1.73–2.26 (4H, m), 2.29 (1H, s), 2.78–2.91 (2H, m), 4.83(1H, m), 7.24 (1H, d, J=8.1), 8.00–8.04 (1H, dd, J=8.1, 2.4), 8.35(1H, d, J=2.4),.; $^{13}$C NMR: δ19.2, 29.9, 32.5, 68.3, 122.7, 124.1, 130.3, 140.9, 145.4.

7-Nitro-3,4-dihydronapthalene. A mixture of 2.89 g(14.9 mmol) of the 1-napthalenol, 3.5 g of amberlyst-15 catio-exchange resin, and 120 mL of benzene was heated at reflux under a nitrogen atmosphere for 2 hours. The reaction mixture was then cooled to room temperature and dried using anhydrous sodium sulfate and filtered. The filtrate was then rotaevaporated to dryness to give the product as an oil in 92% yield. The product was sufficiently pure and was used in the next step without further purification; IR (KBr): 1545; $^1$H NMR: δ2.25–2.36 (2H, m), 2.77–2.86 (2H, t), 6.08–6.17 (1H, m), 6.40–6.45 (1H, m), 7.14 (1H, d, J=8.1), 7.72 (1H, d, J=2.3), 7.83–7.89 (1H, dd, J=8.1, 2.3),.; $^{13}$C NMR: δ23.0, 27.9, 120.6, 122.1, 126.7, 128.6, 131.9, 135.6, 143.5, 147.3.

1,2-Epoxy-7-nitro-1,2,3,4-tetrahydronapthalene. To a solution of 0.5 g (2.85 mmol) of the 7-nitro-3,4-dihydronapthalene in 9 mL of chloroform was added 0.677 g of m-chloroperoxybenzoic acid in one portion. The resulting solution was heated at reflux for 45 minutes. The mixture was then cooled to 0° C. and the precipitated m-chlorobenzoic acid was removed by filtration. The chloroform layer was rotaevaporated to give a pale yellow solid which chromatographed over silica gel (50 g) and eluted with dichloromethane. The relevant fractions were combined and rotaevaporated to give 0.487 g (89.5%) of the epoxide; mp 73–74° C.; IR (KBr): 3300; $^1$H NMR: δ1.70–1.86 (1H, m), 2.42–2.52 (1H, m), 2.54–2.90 (2H, m), 3.75–3.77 (1H, t), 3.91–3.93 (1H, d, J=4.2), 7.22–7.26 (1H, d, J=8.4), 8.05–8.11 (1H, dd, J=8.4, 2.4), 8.24 (1H, d, J=2.4); $^{13}$C NMR: δ21.6, 25.1, 52.3, 55.2, 123.8, 124.8, 129.8, 134.9, 145.0.

7-Nitro-2-tetralone. To a solution of 0.5 g (2.6 mmol) of the above epoxide in 5 mL dry benzene was added 0.37 g (1.1 mmol) of anhydrous zinc iodide. The mixture was stirred at room temperature under nitrogen atmosphere, in the dark. After filtration and removal of solvent under reduced pressure, the resulting yellow oil was taken up into 3 mL of cold absolute ethanol when the product crystallized. Repetitive crystallization from the concentrated mother liquor gave a total yield of 0.415 g(83%); mp 96–97° C.; IR(KBr): 1710, 1330, 1500; $^1$HNMR: δ2.59–2.66 (2H, t), 3.15–3.21 (2H, t), 3.72 (2H, s), 7.38–7.43 (1H, d, J=8.3), 7.98 (1H, d, J =2.2), 8.02–8.03 (1H, dd, J=8.3, 2.2).

Example VIII
Assays—Materials

The plasmid pET11a and the *E. coli* strain BL21(DE3) used for enzyme expression were purchased from Novagen. IPTG was purchased from Sigma. The ECL system used for the Western blotting analysis of bacterial lysates was from Amersham (UK). All the restriction enzymes and Vent polymerase were from New England Biolabs. Mammalian topoisomerase II was isolated from calf thymus glands according to the published procedure (Halligan et al., *J. Biol. Chem.* 260:2475–2482 (1985)). The single copy yeast plasmids YCpGAL1 expressing various topoisomerase I genes in JN2-134 yeast strain were a kind gift of Dr. M-A. Bjornsti (Thomas Jefferson University, Philadelphia, Pa.). All bacterial and yeast media were from Difco (Detroit, Mich.), while cell culture media were purchased from Gibco-BRL (Gaithersburg, Md.).

Example IX
Topoisomerase I Expression in *E. coli*

To obtain large quantity of human topoisomerase I, the human topoisomerase I cDNA was cloned into the pET-11a vector, in which transcription of the cDNA is under the control of the inducible T7 promoter (Studier et al., Methods in Enzymol., Vol. 185:60–89, San Diego: Academic Press (1990)). Briefly, a 3.4 kb DNA fragment containing the entire coding sequence of human topoisomerase I and approximately 1 kb of untranslated region downstream of the stop codon was isolated from the plasmid YCpGAL1-hTOP1 (Bjornsti et al., *Cancer Res.* 49:6318–6323 (1989)) by cutting at the BamHI and EcoRI sites. The vector pET-11a was cut with the same restriction enzymes, dephosphorylated and ligated to the insert in the proper reading frame downstream of the vector cloning site. The ligation mixture was used to transform *E. coli*, the correct clone pET1B was isolated and its identity confirmed by restriction mapping. Since the translational start in pET is positioned at an upstream NdeI site, the expressed topoisomerase I has a 15 amino acid fusion at its N-terminus. pET1B was then transformed into *E. coli* BL21 (DE3), and, upon induction with 0.4 mM IPTG for 1 hour, the bacterial lysate was analyzed by 10% SDS-PAGE. Expression was confirmed by Western blotting using rabbit antibodies against human topoisomerase I. Isolation of the expressed protein was done by a simple procedure. Briefly, *E. coli* cells were lysed by repeated sonic bursts. The sonic extract was made in 1 M NaCl and 6% polyethylene glycol (PEG) to remove nucleic acids. The PEG supernatant was chromatographed directly on a hydroxyapatite column. Expressed human DNA topoisomerase I was eluted at the 0.6 M potassium phosphate step. The eluted enzyme was dialyzed against 50% glycerol, 30 mM potassium phosphate (pH 7.0), 1 mM dithiothreitol (DTT) and 0.1 mM EDTA and stored at −20° C. The relaxation activity of the purified enzyme had a specific activity about 2 orders of magnitude lower than the calf thymus topoisomerase I.

Example X
Expression of Camptothecin-resistant (CPT-K5) Topoisomerase I in *E. coli*.

Two complementary oligonucleotides containing the point mutation CAG (Asp533)->CGG (Gly) responsible for the resistance phenotype in CPT-K5, were synthesized and engineered in the topo I coding sequence using the sequential PCR method (Current Protocols in Molecular Biology, In: Ausubel et al. (eds.), Vol. 1, pp. 8.5.7. Boston:Wiley Interscience (1991)). The two oligonucleotides are 5'-CTTCCTCGGGAA<u>GGG</u>CTCCATCAGATAC-3'(primer X1)(SEQ ID NO:1), and 5'-GTATCTGATGGA<u>GCCC</u>TTCCCGAGGAAG-3'(primer X2)(SEQ ID NO:2), where the underlined sequence represents the mutated codon. Each oligonucleotide was used in separate PCR reactions to amplify two DNA segments adjacent to the mutation site, using the oligonucleotides 5'-ACTGTGAT<u>CCTAGG</u>G-3' ("A")(SEQ ID NO:3) and 5'-CTTCATCGAC<u>AAGCTT</u>GCTCTGAG-3' ("H")(SEQ ID NO:4) as the relative primer pairs for X1 and X2, respectively. "A" and "H" are complementary to the human topo I sequence around the unique restriction sites AvrII and HindIII. After the first round of PCR, the two amplified products X1-H and X2-A were denatured and annealed by their 15 base-pair complementary sequence, due to the overlap of the oligonucleotides X1 and X2. This short stretch of double-stranded DNA segment was then extended by Vent polymerase at 72° C. for 2 minutes to the 748 base pairs full length product A-H. The two external primers "A" and "H" were then used to amplify the full length DNA fragment containing the mutated topo I fragment. The amplified mutant topoisomerase I cDNA was then digested with AvrII and HindIII, and cloned into pET1B by replacing the corresponding AvrII/HindIII fragment in the topoisomerase I cDNA sequence. The plasmid pET1B-CPTK5, which contained the mutant CPT-K5 topoisomerase I cDNA instead of the wildtype human topoisomerase I cDNA, was transformed into E. coli BL21(DE3) for expression. Upon induction with IPTG, the protein in the lysates was confirmed by Western blotting. The CPT-K5 topoisomerase I was then purified from the bacterial lysate as described for the wildtype enzyme.

Example XI
Topo I and Topo II Cleavage Assay

Cleavage assays for the recombinant topoisomerases I and calf thymus topoisomerases I and II were done as described (Liu et al., *J. Biol. Chem.* 258:15365–15370 (1983)). The plasmid YEpG DNA used for the cleavage assays was prepared and labeled at its 3'-end using the published procedures.

Example XII
Yeast Cytotoxicity Assay

It has been established that yeast can survive when topoisomerase I function is obliterated, and that the topoisomerase I poisons only kill cells having a functional topoisomerase I (Bjornsti et al. *Cancer Res.* 49:6318–6323 (1989)). Thus, comparison of the relative extent of growth of each of the test strains in the presence of various drugs with control plates minus drug shows 1) whether the drug has any cytotoxic effects on yeast, 2) whether the cytotoxicity is topo I specific and 3) whether there is any differential specificity of the drug for yeast compared with human topo I.

The topoisomerase I-specific in vivo cytotoxicity assay was adapted from Knab et al. (Knab et al., *J. Biol. Chem.* 268:22322–22330 (1993)). In this system, various topo I genes cloned into the single copy yeast plasmid vector, YCpGAL1 (Knab et al., *J. Biol. Chem.* 268:22322–22330 (1993)), are expressed under the control of the GAL1 promoter in the JN2-134 strain of *S. cerevisiae* (MATa, rad52::LEU2, trp1, ade2-1,his7, ura3-52, ise1, top1-1, leu2) (Bjornsti et al., *Cancer Res.* 49:6318–6323 (1989)). The topo I constructs in the vector are, respectively, the wild-type yeast topo I (YCpGAL-ScTOP1), a non-functional yeast topo I where the active site tyrosine-727 is mutated to a phenylalanine (YCpGAL1-SctoplY727F) (Knab et al., *J. Biol. Chem.* 268:22322–22330 (1993)), and the wild type human topoisomerase I (YCpGAL-hTOP1) (Bjornsti et al., *Cancer Res.* 49:6318–6323 (1989)). To qualitatively test the cytotoxicity and the topo I specificity of the drugs, yeast cells containing the specific plasmid were serially diluted (5-fold) and were grown in dropout medium supplemented with uracil and 2% galactose. In addition, the positive and negative control plates contained: A: Control, no drug in the plate; B: Camptothecin (CPT), 0.5 $\mu$M; C: Coralyne, 1 $\mu$M; D: Methylenedioxy-dihydro-demethyl-coralyne (MDD-Coralyne), 1 $\mu$M, and E: Nitidine, 1 $\mu$M. The plates were grown for 3 days at 30° C. to assess the lethal effect of the different compounds on the various topoisomerase I enzymes expressed in *S. cerevisiae* and the drug being tested.

Example XIII
Cytotoxicity Assay

The $IC_{50}$ of the drugs tested were determined by the MTT-microtiter plate tetrazolinium cytotoxicity assay (MTA) (Mosmann, T., *J. Immunol. Methods* 65:55–63 (1983); Denizot et al., *J. Immunol. Methods* 89:271–277 (1986)). Human lymphoblast RPMI 8402 cells and their camptothecin-resistant CPT-K5 cells (Andoh et al., *Proc. Natl. Acad. Sci., USA* 84:5565–5569 (1987)) were kindly provided by Dr. Toshiwo Andoh (Aichi Cancer Center Research Institute, Nagoya, Japan). The cell lines A2780 and its camptothecin-resistant derivative CPT-2000 were a generous gift of Dr. Jaulang Hwang (Institute of Molecular Biology, Academia sinica, Taiwan). Cells (2000 cells/well, seeded in 200 ml growth medium) were grown in suspension at 37° C. in 5% $CO_2$ and maintained by regular passage in RPMI medium supplemented with 10% heat inactivated fetal bovine serum, L-glutamine (2 mM), penicillin (100 U/mi), and streptomycin (0.1 mg/ml). The cells were exposed continuously for 4 days to drug concentrations ranging from 100 ug/ml to 1.0 ng/ml in ten fold dilutions, and assayed at the end of the fourth day. Each concentration and the no drug control were repeated at least twice in 6 replica wells. The results were plotted and the $IC_{50}$ then measured. The drug sensitive human epidermoid carcinoma KB 3-1 cell line and its vinblastine-selected multidrug-resistant variant KB-V1 cells (Akiyama et al., *Genetics* 11:117–126 (1985)) were kindly provided by Dr. Michael Gottesmann (National Cancer Institute). They were grown as monolayer cultures at 37° C. in 5% $CO_2$ and maintained by regular passage in Dulbecco's minimal essential medium supplemented with 10% heat inactivated fetal bovine serum. KB-V1 cells were maintained in the presence of 1 mg/ml vinblastine.

TABLE 1

Topoisomerase I and Topoisomerase II mediated DNA Cleavage of Coralyne Derivatives and Related Compounds

| Compound | Topo I-mediated DNA cleavage[b] | Topo II-mediated DNA cleavage[c] | Cytotoxicity $IC_{50}$[a] ($\mu$M) Cell Lines RPMI | CPT-K5 |
|---|---|---|---|---|
| Coralyne | 1 | >1000 | 4.9 | 20 |
| Nitidine | 0.1 | 5 | 0.4 | 3.9 |
| MDD-Coralyne | 0.1 | | 8.1 | 27 |
| 6 | >1000 | >1000 | >137 | >137 |
| 7 | >1000 | >1000 | 7.0 | 5.5 |
| 8 | >1000 | >1000 | 6.1 | 12.2 |
| 9 | >1000 | >1000 | 1.2 | 1.2 |
| 13a | 100 | >1000 | 7.1 | 7.1 |
| 13b | 100 | >1000 | 9.0 | 14.9 |
| 13c | 1000 | >1000 | 6.9 | 6.9 |
| 13d | 100 | >1000 | 1.0 | 8.6 |
| 13e | 1.0 | >1000 | 3.0 | 22.4 |
| 13f | 100 | >1000 | 14.2 | 14.2 |
| 13g | 1.0 | >1000 | 20.3 | 13.6 |
| 13j | 10 | >1000 | 9.2 | 15.4 |

TABLE 1-continued

Topoisomerase I and Topoisomerase II mediated DNA
Cleavage of Coralyne Derivatives and Related Compounds

| Com-pound | Topo I-mediated DNA cleavage[b] | Topo II-mediated DNA cleavage[c] | Cytotoxicity $IC_{50}$[a] ($\mu$M) Cell Lines | |
|---|---|---|---|---|
| | | | RPMI | CPT-K5 |
| 14a | 1000 | >1000 | 2.9 | 2.9 |
| 14b | 1000 | >1000 | 4.5 | 7.5 |
| 14c | >1000 | >1000 | 10.4 | 31.1 |
| 14d | 1000 | >1000 | 10.4 | 13.8 |
| 14g | 100 | >1000 | 17.1 | >34 |
| 14j | 1000 | >1000 | >31 | >31 |
| 15a | 100 | >1000 | >24 | >24 |
| 16a | >1000 | >1000 | 25.3 | 23.2 |
| 20 | 100 | >1000 | 16.3 | >33 |
| CPT | 1 | >1000 | 0.004 | >10[d] |
| VM-26 | >1000 | 1 | 0.3 | 0.5 |

[a]$IC_{50}$ has been calculated after 4 days of continuous drug exposure. N.D. = Not determined.
[b]Topoisomerase I cleavage values are reported as REC, Relative Effective Concentration, i.e., concentrations relative to camptothecin (CPT), whose value is arbitrarily assumed as 1, that are able to produce the same cleavage on the plasmid DNA in the presence of human topoisomerase I.
[c]Topoisomerase II cleavage values are reported as REC, Relative Effective Concentration, i.e., concentrations relative to VM-26, whose value is arbitrarily assumed as 1, that are able to produce the same cleavage on the plasmid DNA in the presence of calf thymus topoisomerase II.
[d]No indication of cytotoxicity were considered indicative of $1C_{50}$ values substantially greater than the highest doses assayed Certain compounds of formula I, in particular, comound 13e, are potent topoisomerase I poisions. Additionally, compounds of formula I generally possess cytotoxic activity against RPMI 8402 cancer cells and camptothecin resistant CPT-K5 cells. Accordingly, compounds of formula I may be useful as cytotoxic agents, for the treatment of cancers, in particular, the solid mammalian tumors or hematologic malignancies identified herein above.

The fact that benz[a]acridines are non-charged analogs related to coralyne suggests that these agents may have enhanced cell absorption. There is also the potential that they may be less readily cleared than charged compounds in vivo. In addition, the absence of the benzisoquinolium moiety, which is present within the structure of coralyne and coralyne analogs, may result in these analogs having less neurotoxicity.

All publications, patents and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

We claim:

1. A compound of formula II:

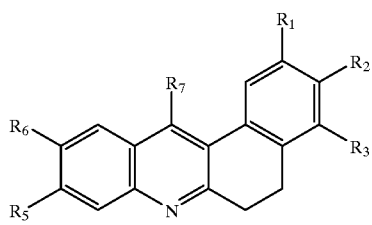

(II)

wherein $R_1$ and $R_2$ are independently OH, $NO_2$, $NH_2$, halo, $NHCO(C_1-C_8)$alkyl or $(C_1-C_8)$alkoxy; or $R_1$ and $R_2$ together are —$OCH_2O$—;

$R_3$ is H;

$R_5$ and $R_6$ are independently H, OH, $NO_2$, $NH_2$, halo, $NHCO(C_1-C_8)$alkyl or $(C_1-C_8)$alkoxy; or $R_5$ and $R_6$ together are —$OCH_2O$—; and $R_7$ is H, or $(C_1-C_8)$alkyl;

or a pharmaceutically acceptable salt thereof.

2. A compound of the formula:

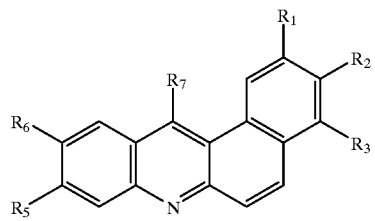

wherein $R_1$ and $R_2$ are independently $NO_2$, halo, $NHCO(C_1-C_8)$alkyl or $(C_1-C_8)$alkoxy; or $R_1$ and $R_2$ together are —$OCH_2O$—;

$R_3$ is H;

$R_5$ and $R_6$ are independently H, OH, $NO_2$, $NH_2$, halo, $NHCO(C_1-C_8)$alkyl or $(C_1-C_8)$alkoxy; or $R_5$ and $R_6$ together are —$OCH_2O$—; and $R_7$ is H, or $(C_1-C_8)$alkyl;

or a pharmaceutically acceptable salt thereof.

3. A compound of claim 1 or 2 wherein one or both $R_1$ and $R_2$ are $(C_1-C_8)$alkoxy.

4. A compound of claim 1 or 2 wherein both of $R_1$ and $R_2$ are $(C_1-C_8)$alkoxy.

5. A compound of claim 1 or 2 wherein one or both $R_1$ and $R_2$ are methoxy.

6. A compound of claim 1 or 2 wherein $R_1$ and $R_2$ are both methoxy.

7. A compound of claim 1 or 2 wherein $R_1$ and $R_2$ together are —$OCH_2O$—.

8. A compound of claim 1 or 2 wherein $R_5$ and $R_6$ together are —$OCH_2O$—.

9. A compound of claim 1 or 2 wherein $R_5$ and $R_6$ are each independently OH or ($C_1$–$C_8$)alkoxy; or $R_5$ and $R_6$ together are —$OCH_2O$—.

10. A compound of claim 1 or 2 wherein $R_7$ is hydrogen, methyl, or ethyl.

11. A compound of formula II:

(II)

wherein $R_1$, $R_2$, $R_3$, $R_5$ and $R_6$ are independently H, OH, $NO_2$, $NH_2$, halo, NHCO($C_1$–$C_8$)alkyl or ($C_1$–$C_8$)alkoxy; $R_1$ and $R_2$ together are —$OCH_2O$—; $R_2$ and $R_3$ together are —$OCH_2O$—; $R_5$ and $R_6$ together are —$OCH_2O$—; and $R_7$ is H, or ($C_1$–$C_8$)alkyl;

or a pharmaceutically acceptable salt thereof; provided one or both of $R_1$ and $R_2$ is ($C_1$–$C_8$)alkoxy or $R_1$ and $R_2$ together are —$OCH_2O$—.

12. A compound of the formula:

wherein $R_1$, $R_2$, $R_3$, $R_5$ and $R_6$ are independently H, OH, $NO_2$, $NH_2$, halo, NHCO($C_1$–$C_8$)alkyl or ($C_1$–$C_8$)alkoxy; $R_1$ and $R_2$ together are —$OCH_2O$—; $R_2$ and $R_3$ together are —$OCH_2O$—; or $R_5$ and $R_6$ together are —$OCH_2O$—; and $R_7$ is H, or ($C_1$–$C_8$)alkyl;

or a pharmaceutically acceptable salt thereof; provided one or both of $R_1$ and $R_2$ is ($C_1$–$C_8$)alkoxy or $R_1$ and $R_2$ together are —$OCH_2O$—.

13. A compound of claim 11 or 12 wherein $R_5$ and $R_6$ are each independently OH or ($C_1$–$C_8$)alkoxy; or $R_5$ and $R_6$ together are —$OCH_2O$—.

14. A compound of claim 11 or 12 wherein $R_7$ is hydrogen, methyl, or ethyl.

15. A compound of claim 11 or 12 wherein $R_2$ and $R_3$ together are —$OCH_2O$—.

16. A compound of formula II:

(II)

wherein $R_1$, $R_5$ and $R_6$ are independently H, OH, $NO_2$, $NH_2$, halo, NHCO($C_1$–$C_8$)alkyl or ($C_1$–$C_8$)alkoxy;

$R_2$ and $R_3$ together are —$OCH_2O$—; and $R_7$ is H, or ($C_1$–$C_8$)alkyl;

or a pharmaceutically acceptable salt thereof.

17. A compound of the formula:

wherein $R_1$, $R_5$ and $R_6$ are independently H, OH, $NO_2$, $NH_2$, halo, NHCO($C_1$–$C_8$)alkyl or ($C_1$–$C_8$)alkoxy;

$R_2$ and $R_3$ together are —$OCH_2O$—; and $R_7$ is H, or ($C_1$–$C_8$)alkyl;

or a pharmaceutically acceptable salt thereof.

18. A compound of claim 16 or 17 wherein $R_5$ and $R_6$ are each independently OH or ($C_1$–$C_8$)alkoxy.

19. A compound of claim 16 or 17 wherein $R_5$ and $R_6$ are each methoxy.

20. A compound of claim 16 or 17 wherein $R_7$ is hydrogen, methyl, or ethyl.

21. The compound 2,3,9,10-tetramethoxy-5,6-dihydrobenz[a]acridine; 2,3,-dimethoxy-9,10-methylenedioxy-5,6-dihydrobenz[a]acridine; 2,3-dimethoxy-5,6-dihydrobenz[a]acridine; 5,6-dihydro-9,10-dimethoxy -3,4-methylenedioxybenz[a]acridine; 5,6-dihydro-3,4,9,10-tetramethoxybenz[a]acridine; 2-amino-9,10-dimethoxy-5,6-dihydrobenz[a]acridine; 3-chloro-9,10dimethoxy -5,6-dihydrobenz[a]acridine; 2,3,9,10-Tetramethoxybenz[a]acridine; 2,3,-Dimethoxy -9,10-methylenedioxybenz[a]acridine; 9,10-Dimethoxybenz[a]acridine; 2,3-Dimethoxy-benz[a]acridine; 3-Chloro-9,10-dimethoxybenz[a]acridine; 2,3,9,10-Tetramethoxy-7-methyl -5,6-dihydrobenz[a]acridinium methosulfate; 2,3,9,10-Tetramethoxy-7-methylbenz[a]acridinium methosulfate; 2,3,9,10-tetrahydroxy-5,6-dihydrobenz[a]acridine; or 2,3,9,10-tetrahydroxybenz[a]acridine; or a pharmaceutically acceptable salt thereof.

22. The compound 5,6-dihydro-9,10-dimethoxy-3,4-methylenedioxybenz[a]-acridine; or a pharmaceutically acceptable salt thereof.

23. A pharmaceutical composition comprising a compound of claim 22, 1, 2, 11, 12, 16, or 17 in combination with a pharmaceutically acceptable carrier.

24. A therapeutic method to inhibit cancer cell growth comprising administering to a mammal afflicted with cancer an effective amount of a compound of claim 22, 1, 1, 11, 12, 16 or 17.

25. The method of claim 24 wherein the mammal is a human.

26. The method of claim 25 wherein the cancer is a leukemia or melanoma.

27. The method of claim 26 wherein the cancer is a solid tumor.

28. The method of claim 27 wherein the tumor is a breast, lung, colon, or ovarian tumor.

29. The method of claim 24 wherein the compound is administered in combination with a pharmaceutically acceptable carrier.

* * * * *

```
                         SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
          (A) LENGTH: 28 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO:1:

CTTCCTCGGG AAGGGCTCCA TCAGATAC                                        28

(2) INFORMATION FOR SEQ ID NO:2:

(i) SEQUENCE CHARACTERISTICS:
          (A) LENGTH: 28 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO:2:
```

```
GTATCTGATG GAGCCCTTCC CGAGGAAG                                    28

(2) INFORMATION FOR SEQ ID NO:3:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

ACTGTGATCC TAGGG                                                  15

(2) INFORMATION FOR SEQ ID NO:4:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

CTTCATCGAC AAGCTTGCTC TGAG                                        24
```